(12) United States Patent
Nakamura et al.

(10) Patent No.: US 8,358,734 B2
(45) Date of Patent: Jan. 22, 2013

(54) X-RAY COMPUTERIZED TOMOGRAPHY APPARATUS, BREATHING INDICATION APPARATUS AND MEDICAL IMAGING APPARATUS

(75) Inventors: Hitoshi Nakamura, Otawara (JP); Masaharu Tsuyuki, Nasushiobara (JP); Tatsuo Maeda, Otawara (JP); Shan shan Xiao, Dalian (CN)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/625,836

(22) Filed: Nov. 25, 2009

(65) Prior Publication Data

US 2010/0074394 A1 Mar. 25, 2010

Related U.S. Application Data

(62) Division of application No. 11/870,633, filed on Oct. 11, 2007.

(30) Foreign Application Priority Data

Oct. 11, 2006 (JP) .................................. 2006-277886
Oct. 17, 2006 (JP) .................................. 2006-282844
Oct. 17, 2006 (JP) .................................. 2006-282845

(51) Int. Cl.
*H05G 1/62* (2006.01)
(52) U.S. Cl. ............................... 378/8; 378/95; 378/115
(58) Field of Classification Search ................ 378/8, 95, 378/115
See application file for complete search history.

(56) References Cited

U.S. PATENT DOCUMENTS

| | | | | |
|---|---|---|---|---|
| 5,619,995 A | * | 4/1997 | Lobodzinski | 600/425 |
| 5,901,200 A | * | 5/1999 | Krause | 378/198 |
| 6,510,337 B1 | * | 1/2003 | Heuscher et al. | 600/428 |
| 6,763,082 B2 | * | 7/2004 | Ozaki | 378/8 |
| 6,937,696 B1 | | 8/2005 | Mostafavi | |
| 7,050,537 B2 | | 5/2006 | Tsujii | |
| 7,177,386 B2 | | 2/2007 | Mostafavi et al. | |
| 7,182,083 B2 | * | 2/2007 | Yanof et al. | 128/204.23 |
| 7,251,308 B2 | * | 7/2007 | Tsuyuki | 378/8 |
| 7,502,445 B2 | * | 3/2009 | Shi et al. | 378/115 |

(Continued)

FOREIGN PATENT DOCUMENTS

JP 2003-265464 9/2003

(Continued)

OTHER PUBLICATIONS

Japanese Office Action issued May 22, 2012, in Patent Application No. 2007-260322 (with English-language translation).

(Continued)

*Primary Examiner* — Thomas R Artman
(74) *Attorney, Agent, or Firm* — Oblon, Spivak, McClelland, Maier & Neustadt, L.L.P.

(57) ABSTRACT

An X-ray computed tomographic apparatus includes a gantry 100 including an X-ray tube 101 which generates X-rays and an X-ray detector 103 which detects X-rays transmitted through a subject to be examined, a reconstruction device 114 which generates tomogram data on the basis of an output from the X-ray detector, a breath detector 203 which detects a respiration waveform representing a temporal change in respiration index value associated with the subject, a regular respiration waveform generating unit 207 which generates a respiration waveform with a regular respiration cycle which originates from the detected respiration waveform, and a gantry mount display 201 which displays the generated regular respiration waveform.

3 Claims, 22 Drawing Sheets

U.S. PATENT DOCUMENTS

| | | | |
|---|---|---|---|
| 7,715,520 B2* | 5/2010 | Nagata et al. | 378/8 |
| 2004/0077941 A1* | 4/2004 | Reddy et al. | 600/428 |
| 2004/0179644 A1* | 9/2004 | Tsuyuki | 378/8 |
| 2005/0089133 A1* | 4/2005 | Tsuyuki | 378/8 |
| 2005/0119560 A1 | 6/2005 | Mostafavi | |
| 2006/0074305 A1 | 4/2006 | Mostafavi | |
| 2007/0053486 A1* | 3/2007 | Zelnik et al. | 378/20 |
| 2008/0056547 A1* | 3/2008 | Kokubun et al. | 382/128 |
| 2008/0123812 A1 | 5/2008 | Sabol et al. | |

FOREIGN PATENT DOCUMENTS

| | | |
|---|---|---|
| JP | 2004-533889 | 11/2004 |
| JP | 2005-074156 | 3/2005 |
| JP | 2008-514371 | 5/2008 |

OTHER PUBLICATIONS

Office Action mailed Oct. 16, 2012 in Japanese Patent Application No. 2007-260322 (with English Translation).

* cited by examiner

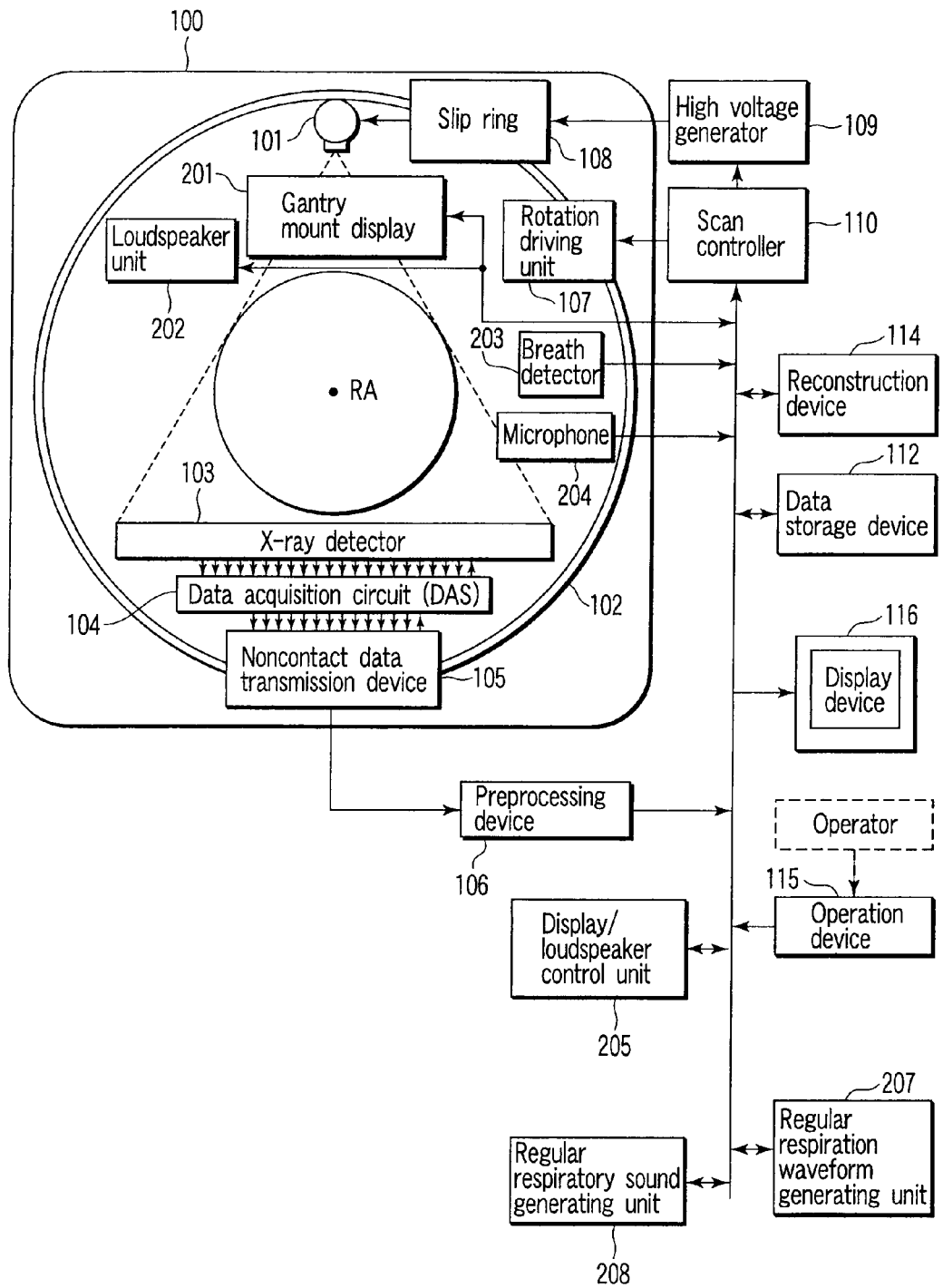
F I G. 1

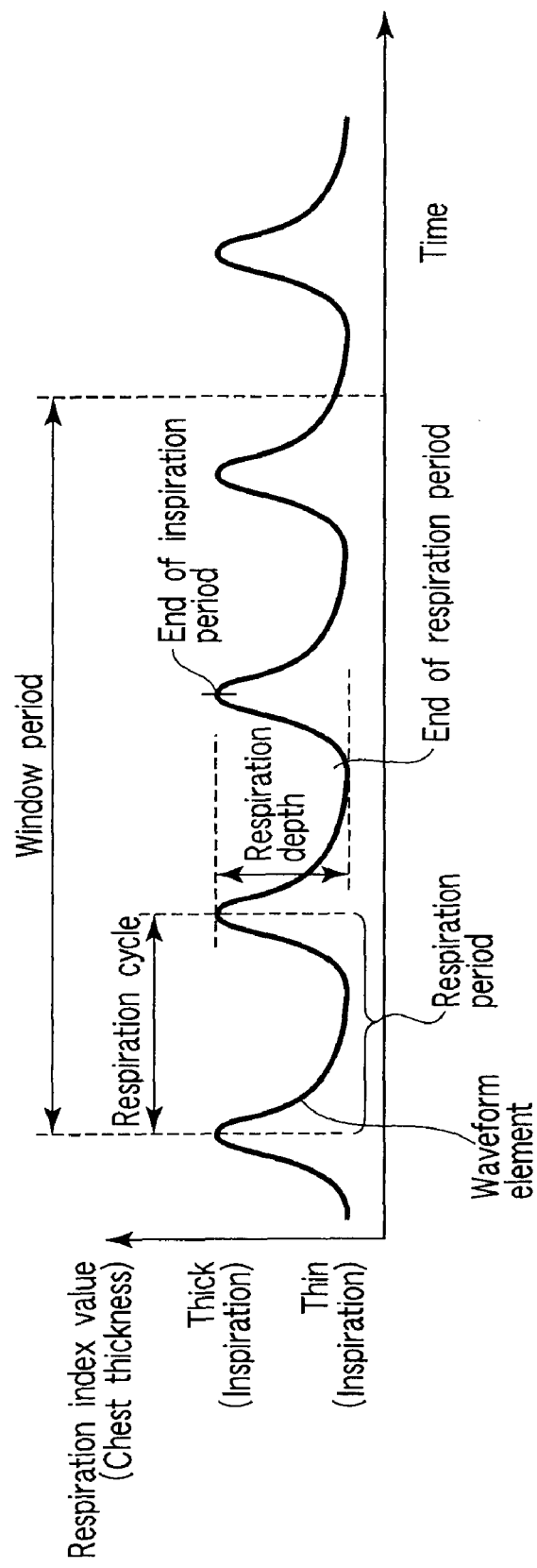
F I G. 4

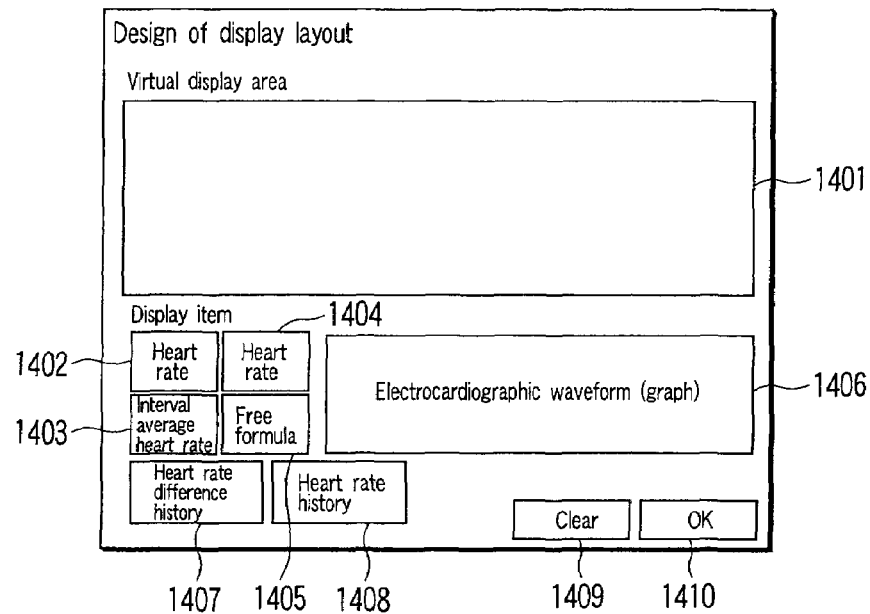
F I G. 14
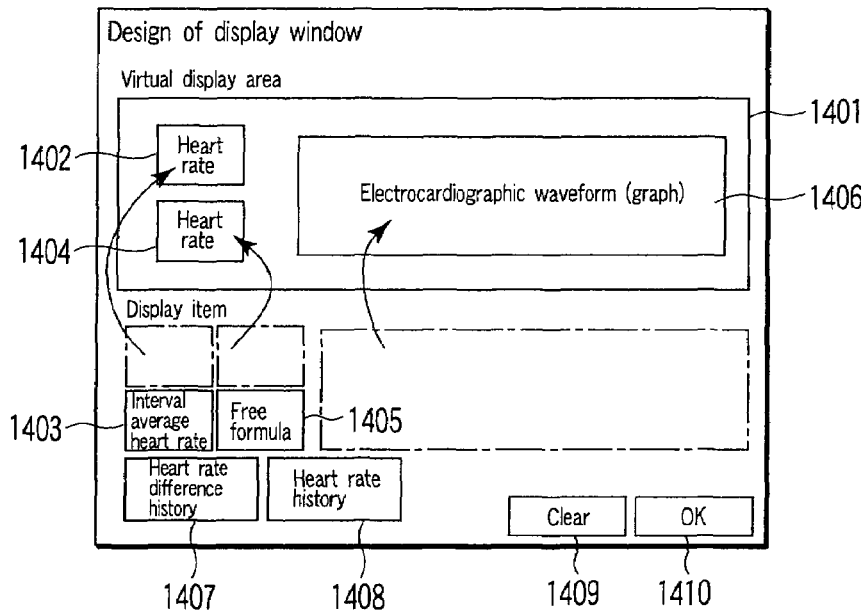
F I G. 15

20 seconds before start of breath holding 1-1

Breathe deeply and hold 1-2-1

1-2-2

Keep holding your breath 1-3-1

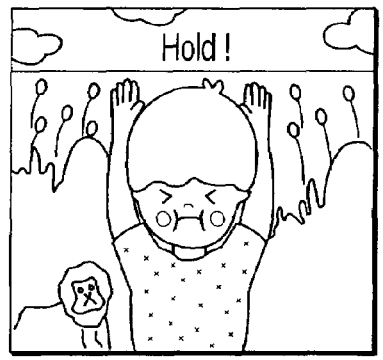
FIG. 25
15 seconds before start of breath holding  1-4
FIG. 26
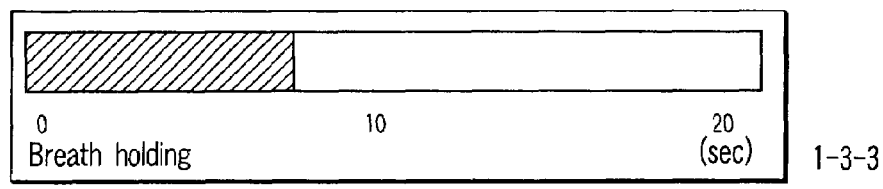
FIG. 27
Stop holding your breath and make yourself relax  1-5-1
FIG. 28

35 seconds before
next scan
2-1
FIG. 29
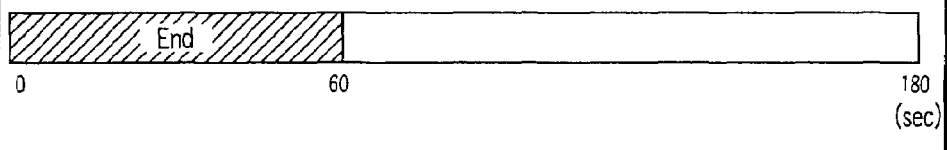
3-1
FIG. 30
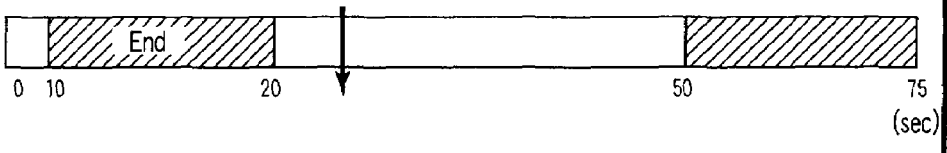
3-2
FIG. 31

```
Loudspeaker output list
1-1) Audio 1          2-1) Track 1 of memory device
1-2) Audio 2          2-2) Track 2 of memory device
1-3) Audio 3          2-3) Track 3 of memory device
  •                   2-4) Track 4 of memory device
  •
  •                   3-1) Microphone 1
                      3-2) Microphone 2
                                                    8-1
```

FIG. 37

```
20 seconds after
start of scan
                  9-1
```

FIG. 38

```
During scan 9-2
```

FIG. 39

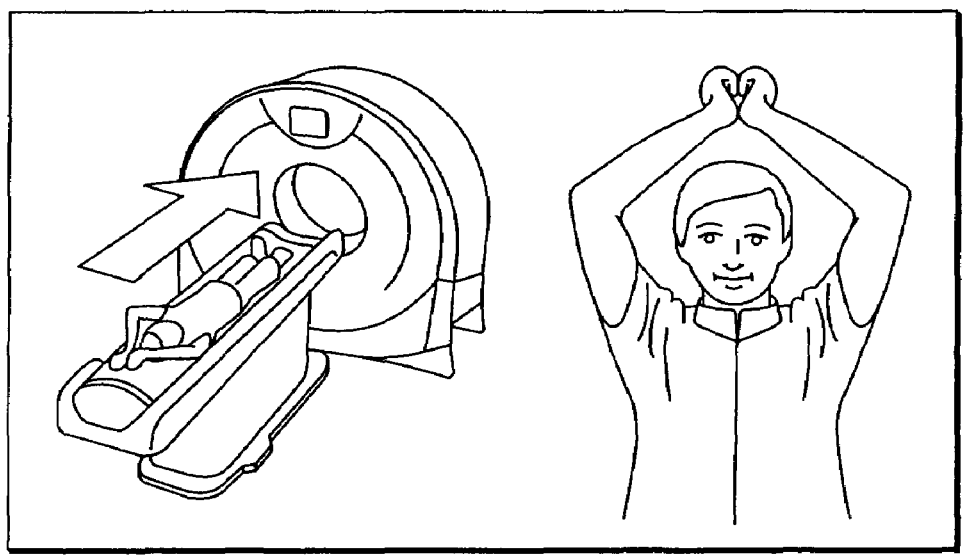
F I G. 44

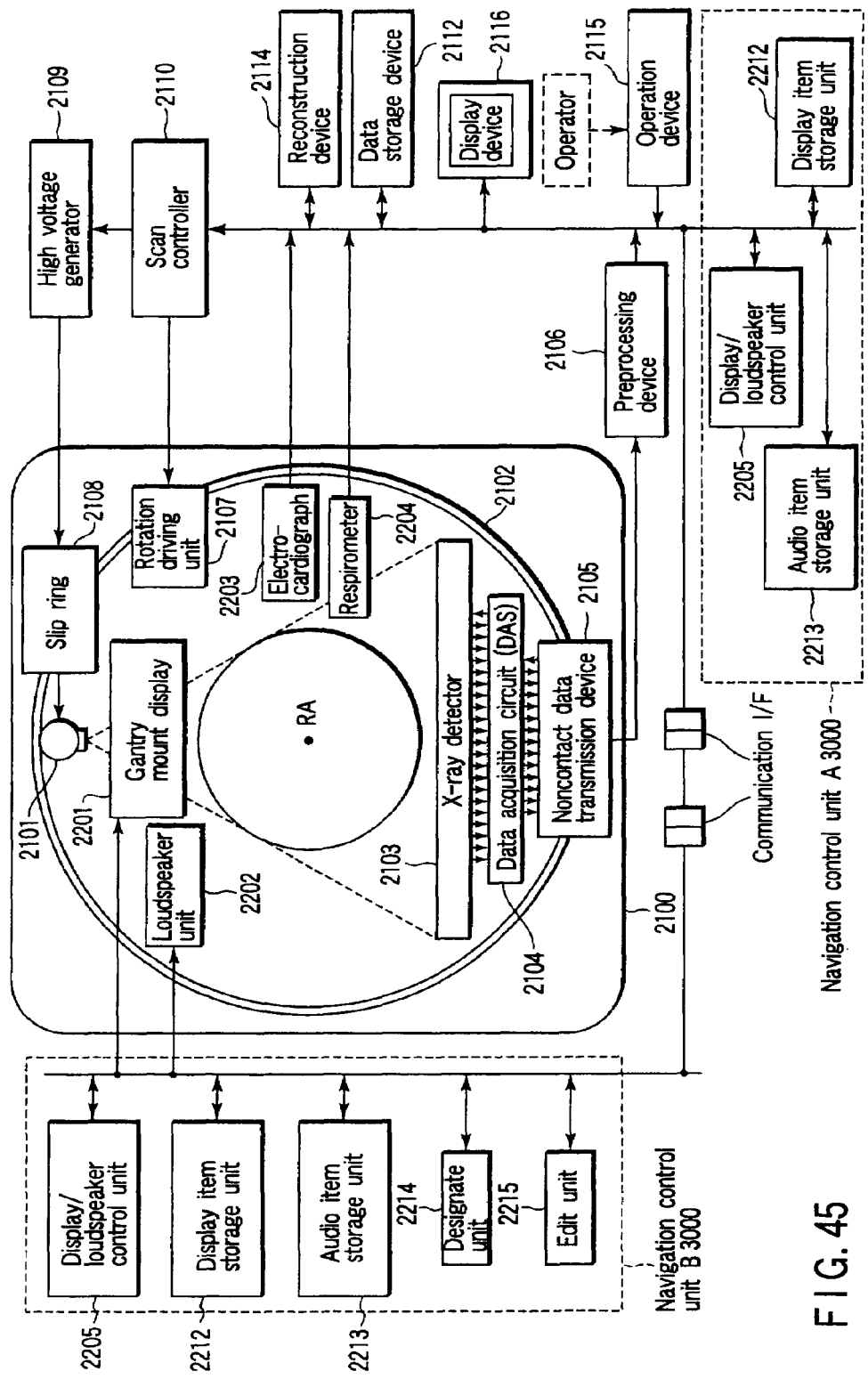
F I G. 45

X-RAY COMPUTERIZED TOMOGRAPHY APPARATUS, BREATHING INDICATION APPARATUS AND MEDICAL IMAGING APPARATUS

CROSS-REFERENCE TO RELATED APPLICATIONS

This application is a division of and claims the benefit of priority under 35 U.S.C. §120 from U.S. Ser. No. 11/870,633 filed Oct. 11, 2007, and claims the benefit of priority under 35 U.S.C. §119 from Japanese Patent Application Nos. 2006-277886 filed Oct. 11, 2006; No. 2006-282844 filed Oct. 17, 2006; and No. 2006-282845 filed Oct. 17, 2006, the entire contents of each of which are incorporated herein by reference.

BACKGROUND OF THE INVENTION

1. Field of the Invention

The present invention relates to an X-ray computed tomographic apparatus, breath instruction apparatus, and medical imaging apparatus which generate medical images by imaging a subject to be examined.

2. Description of the Related Art

Stable breathing is indispensable for improving image quality by reducing artifacts. Conventionally, in order to stabilize breathing motion, an operator gives a subject to be examined spoken instructions from an operator room through a microphone. It is, however, difficult to stabilize breathing motion by spoken instructions. Furthermore, an operator who has not comprehended the stable breathing of a subject may unstabilize the breathing of the subject by giving him/her inappropriate instructions. See Jpn. Pat. Appln. KOKAI Publication No. 2003-265464.

Conventionally, an X-ray computed tomographic apparatus uses an imaging method and reconstruction method which require the electrocardiographic complex of a subject, such as an ECG-gated scanning method and an ECG-gated reconstruction method. However, a conventional X-ray computed tomographic apparatus does not allow to check how electrocardiograms have been captured, and hence may not be properly ECG-gated. In operation except ECG-gated imaging or ECG-gated reconstruction, it is preferable in terms of reduction in artifacts to perform scanning in a period during which the heart rate is stable. It is, however, impossible to check this. The operator therefore starts scanning upon determining a stable period by checking the heart rate according to his/her experience. See Jpn. Pat. Appln. KOKAI Publication No. 2003-265464.

In addition, conventionally, a subject is instructed by voice how to act during examination. For example, the automatic voice playback device of an apparatus gives a spoken instruction to hold a breath or a spoken instruction not to move, or the operator gives such instructions by human voice through a microphone. The subject totally depends on voice when acquiring information, and cannot know any information about the remaining time of breath holding, the remaining time of examination, and the like without voice. This may cause a situation in which the subject feels insecure. In addition, in imaging operation, it is preferable in term of reduction in body movement artifacts that a subject keeps quiet and relaxed and stabilizes his/her heartbeat and breath as much as possible. However, conventional apparatuses have not been provided with any techniques for making subjects feel relaxed. See Jpn. Pat. Appln. KOKAI Publication No. 2003-265464.

BRIEF SUMMARY OF THE INVENTION

It is an object of the present invention to promote stabilizing the breathing motion of a subject to be examined.

It is another object of the present invention to provide information which allows to objectively check how electrocardiograms are captured or the cardiac motion is stabilized.

An X-ray computed tomographic apparatus in accordance with first aspect of the present invention includes a gantry including an X-ray tube which generates X-rays and an X-ray detector which detects X-rays transmitted through a subject to be examined, a reconstruction device which generates tomogram data on the basis of an output from the X-ray detector, a breath detector which detects a respiration waveform representing a temporal change in respiration index value associated with the subject, a regular respiration waveform generating unit which generates a respiration waveform with a regular respiration cycle which originates from the detected respiration waveform, and a gantry mount display which displays the generated regular respiration waveform.

A medical imaging apparatus in accordance with second aspect of the present invention includes an image generating unit which generates image data by imaging a subject to be examined; a breath detecting unit which detects a respiration waveform representing a temporal change in respiration index value associated with the subject; a regular respiration waveform generating unit which generates a respiration waveform with a regular respiration cycle which originates from the detected respiration waveform; and a breath instruction unit which provides breath instruction information on the basis of the generated regular respiration waveform.

A breath instruction apparatus in accordance with third aspect of the present invention includes a breath detecting unit which detects a respiration waveform representing a temporal change in respiration index value associated with a subject to be examined; a regular respiration waveform generating unit which generates a respiration waveform with a regular respiration cycle which originates from the detected respiration waveform; and a display unit which displays the generated regular respiration waveform.

An X-ray computed tomographic apparatus in accordance with fourth aspect of the present invention includes a gantry including an X-ray tube which generates X-rays and an X-ray detector which detects X-rays transmitted through a subject to be examined; a tomogram generating unit which generates tomogram data on the basis of an output from the X-ray detector; a cardiac index calculating unit which instantly calculates a plurality of cardiac indexes associated with a heartbeat state on the basis of an electrocardiogram associated with the subject; a cardiac index selection unit which selects at least one cardiac index among the plurality of calculated cardiac indexes in accordance with a user instruction; and a display unit which is held on a housing of the gantry directly or through an arm and instantly displays the selected cardiac index.

An X-ray computed tomographic apparatus in accordance with fifth aspect of the present invention includes a gantry including an X-ray tube which generates X-rays and an X-ray detector which detects X-rays transmitted through a subject to be examined; a tomogram generating unit which generates tomogram data on the basis of an output from the X-ray detector; a file storage unit which stores a plurality of audio files and a plurality of image files which are associated with instructions to the subject; an information storage unit which stores information associating the audio file and the image file with each of a plurality of examination stages; an instruction information providing unit which provides instruction information to the subject on the basis of the audio file and the image file which are associated with an examination stage in accordance with a progress of the examination; and a changing unit which changes the association information in accordance with a user instruction.

A medical imaging apparatus in accordance with sixth aspect of the present invention includes an image generating unit which generates image data by imaging a subject to be examined; a file storage unit which stores a plurality of audio files and a plurality of image files which are associated with instructions to the subject; an information storage unit which stores information associating the audio file and the image file with each of a plurality of examination stages; an instruction information providing unit which provides instruction information to the subject on the basis of the audio file and the image file which are associated with an examination stage in accordance with a progress of the examination; and a changing unit which changes the association information in accordance with a user instruction.

An X-ray computed tomographic apparatus in accordance with seventh aspect of the present invention includes, which scans a subject to be examined with X-rays, acquires projection data, and reconstructs an image, and a respiration navigation apparatus which guides respiration operation for the subject, the respiration navigation apparatus including a storage unit which stores a plurality of respiration guide data files for guiding the respiration operation, a read control unit which selectively reads out the respiration guide data file from the storage unit in accordance with a control signal from the X-ray computed tomographic apparatus, and a display unit which displays the readout respiration guide data file, and the X-ray computed tomographic apparatus including a control signal generating unit which controls scanning of the subject and generates the control signal in synchronism with control on the scanning, and a display unit which displays a time of generation of the control signal, a type of the control signal, and an execution result.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a block diagram showing the arrangement of an X-ray computed tomographic apparatus according to an embodiment of the present invention;

FIG. 4 is a timing chart showing an example of a respiration waveform detected by a breath detector in FIG. 1;

FIG. 14 is a view showing a display layout design window example provided by the display layout support unit in FIG. 9;

FIG. 15 is a view showing an example of operation on the display layout design window in FIG. 14;

FIG. 25 is a view showing still another example of the display item stored in the display item storage unit in FIG. 16;

FIG. 26 is a view showing still another example of the display item stored in the display item storage unit in FIG. 16;

FIG. 27 is a view showing still another example of the display item stored in the display item storage unit in FIG. 16;

FIG. 28 is a view showing still another example of the display item stored in the display item storage unit in FIG. 16;

FIG. 29 is a view showing still another example of the display item stored in the display item storage unit in FIG. 16;

FIG. 30 is a view showing still another example of the display item stored in the display item storage unit in FIG. 16;

FIG. 31 is a view showing still another example of the display item stored in the display item storage unit in FIG. 16;

FIG. 37 is a view showing still another example of the display item stored in the display item storage unit in FIG. 16;

FIG. 38 is a view showing still another example of the display item stored in the display item storage unit in FIG. 16;

FIG. 39 is a view showing still another example of the display item stored in the display item storage unit in FIG. 16;

FIG. 44 is a view showing an example of an image indicating the progress of examination;

FIG. 45 is a block diagram showing a user navigation system as a modification, together with an X-ray CT apparatus.

DETAILED DESCRIPTION OF THE INVENTION

First Embodiment

Figure 2:
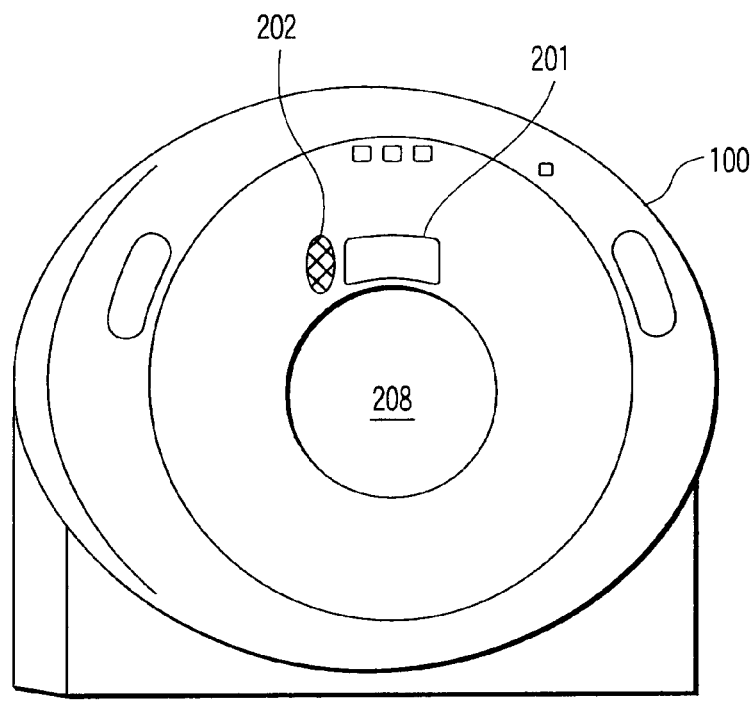
FIG. 2 is a view showing the mount position of a gantry mount display in FIG. 1 on a gantry.

An embodiment of an X-ray computed tomographic apparatus according to the present invention will be described below with reference to the views of the accompanying drawing. Note that the present invention is not limited to an X-ray computed tomographic apparatus and can be applied to other medical imaging apparatuses which generate images associated with a subject to be examined, e.g., an X-ray diagnostic apparatus, magnetic resonance imaging apparatus (MRI), ultrasonic diagnostic apparatus, and gamma camera. The present invention can also be applied to a breath instruction apparatus specialized as a breath instruction function. An X-ray computed tomographic apparatus will be exemplified below. Note that X-ray computed tomographic apparatuses include various types of apparatuses, e.g., a rotate/rotate-type apparatus in which an X-ray tube and an X-ray detector rotate together around a subject to be examined, and a stationary/rotate-type apparatus in which many detection elements are arrayed in the form of a ring, and only an X-ray tube rotates around a subject to be examined. The present invention can be applied to either type. In this case, the rotate/rotate type, which is currently the mainstream, will be exemplified. In order to reconstruct one-slice tomogram data, projection data corresponding to one rotation around a subject to be examined, i.e., about 360°, is required, or (180°+view angle) projection data is required in the half scan method. The present invention can be applied to either of these reconstruction schemes. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. As an X-ray detection element, either of these schemes can be used. In this case, the former type, i.e., the indirect conversion type, will be exemplified. Recently, with advances toward the commercialization of a so-called multi-tube type X-ray computed tomographic apparatus having a plurality of pairs of X-ray tubes and X-ray detectors mounted on a rotating ring, related techniques have been developed. The present invention can be applied to both a conventional single-tube type X-ray computed tomographic apparatus and a multi-tube type X-ray computed tomographic apparatus. The single-tube type X-ray computed tomographic apparatus will be exemplified here.

FIG. 1 shows the arrangement of the main part of an X-ray computed tomographic apparatus according to this embodiment. The X-ray computed tomographic apparatus according to this embodiment includes a gantry 100. The gantry 100 includes an annular rotating frame 102. A rotation driving unit 107 drives/rotates the rotating frame 102 about a rotation axis RA. An X-ray tube 101 and an X-ray detector 103 are mounted on the rotating frame 102. The X-ray tube 101 faces the X-ray detector 103 through the rotation axis RA. The X-ray tube 101 receives a tube voltage and filament current from a high voltage generator 109 through a slip ring 108, and generates X-rays. The X-ray detector 103 detects X-rays transmitted through the subject and outputs an electrical signal reflecting the dose of incident X-rays. A preprocessing device 106 receives a signal (pure raw data) output from the X-ray detector 103 through a data acquisition circuit 104 and a noncontact data transmission device 105. In the preprocessing device 106, a data storage device 112 stores data having undergone sensitivity correction, logarithmic transformation, and the like (called projection data or raw data).

A breath detector 203 and a microphone 204 are provided on or near the gantry 100. The breath detector 203 detects the breathing motion of the subject and outputs data associated with a respiration index value or equivalent data (to be simply referred to as breath data hereinafter). The data storage device 112 stores the breath data. Various kinds of breath detection methods, e.g., methods of measuring a respiratory flow rate and flow, are available. Assume that in this embodiment, a method using the thickness of the chest of a subject which periodically changes in accordance with breathing motion is used as a simple method in which the psychological burden on the subject is light. The microphone 204 is provided to detect mainly the respiratory sound of the subject. This respiratory sound is recorded and played back as a respiration guide through a loudspeaker unit 202 together with the display of a regular respiration waveform.

Figure 3:
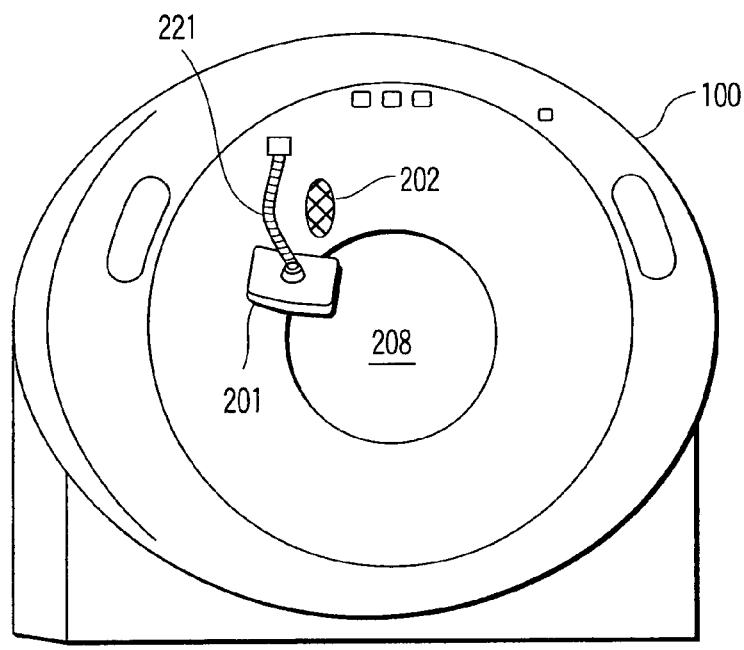
FIG. 3 is a view showing another example of the mount position of the gantry mount display in FIG. 1 on the gantry.

A gantry mount display 201 is placed on or near the gantry 100. More specifically, as shown in FIG. 2, the gantry mount display 201 comprising a liquid crystal panel and the like is placed on the housing surface of the gantry 100 at a position where the display does not become an X-ray blockage and can be visually recognized by the subject inserted into an opening portion 208, typically a cone-shaped portion around the opening portion 208. As shown in FIG. 3, the gantry mount display 201 may be suspended from the gantry 100 through an articulated arm 221. The gantry loudspeaker unit 202 is placed on or near the gantry 100. More specifically, the gantry loudspeaker unit 202 is placed on the housing surface of the gantry 100 at a position where the loudspeaker unit does not become an X-ray blockage and the subject inserted in the opening portion can easily hear, typically a cone-shaped portion around the opening portion.

A scan controller 110 controls the operations of the rotation driving unit 107, high voltage generator 109, and the like to perform data acquisition (scanning). A reconstruction device 114 reconstructs tomogram data on the basis of projection data stored in the data storage device 112. The display device 116 is provided to display mainly tomogram data. An operation device 115 comprises a keyboard, mouse, and the like and is used to input operator instructions.

A display/loudspeaker control unit 205 controls the display of a regular respiration waveform generated by a regular respiration waveform generating unit 207 on the gantry mount display 201 and the playback output of regular respiratory sound corresponding to the regular respiration waveform generated by a regular respiratory sound generating unit 208 from the gantry loudspeaker unit 202. This embodiment is characterized in that a regular respiration waveform is generated and presented to the subject, and respiratory sound (regular respiratory sound) corresponding to the regular respiration waveform is played back to promote stabilizing the breathing motion of the subject.

FIG. 4 shows an example of a respiration waveform detected by the breath detector 203. The chest thickness as a respiration index value rapidly increases in an inspiration period, becomes maximum at the end of the inspiration period, gradually decreases in an expiration period, and becomes minimum at the end of the expiration period. In this case, the period from the end of an inspiration period to the end of the next inspiration period is called a respiration period as a unit period, and its time width is defined as a respiration cycle. A partial waveform in one respiration period is defined as a waveform element as a minimum unit of a respiration waveform. In addition, in this embodiment, a period from the end of an inspiration period to the lapse of a predetermined fixed time is defined as a window period for determining whether breathing motion is stable. Part of a respiration waveform included in this window period will be referred to as a waveform portion. Furthermore, a change in chest thickness due to breathing motion, i.e., the difference between the chest thickness (maximum thickness) at the end of an inspiration period and the chest thickness (minimum thickness) at the end of an expiration period, will be referred to as a respiration depth. As will be described later, a respiration depth is calculated for each respiration period.

As described above, a characteristic feature of this embodiment is to present a regular respiration waveform. A regular respiration waveform is a respiration waveform exhibiting that a respiration cycle and variations in respiration cycle due to a unique respiration waveform generated by a subject by himself/herself in a period during which the subject stably repeats breathing are constant and regular. Essentially, a regular respiration waveform is a waveform with which the subject can perform breathing motion most comfortably. It is especially important to generate a regular respiration waveform from the respiration waveform of the subject himself/herself. Such a waveform can reflect the peculiar way and manner of breathing unique to the subject. This greatly improves the effect of promoting stabilizing breathing motion as compared with a case wherein a so-called generalized respiration waveform is presented upon simple expansion or contraction.

This embodiment presents three kinds of methods of generating regular respiration waveforms as will be described below. In practice, the regular respiration waveform generating unit 207 uses an arbitrary one of the generation methods by selectively executing three kinds of program codes corresponding to the three kinds of generation methods in accordance with an operator instruction. The three kinds of methods of generating regular respiration waveforms will be sequentially described below. Before the generation of a regular respiration waveform, the breath detector 203 detects the breath of the subject, and the data storage device 112 stores, for example, respiration data for several min. In the same period, the microphone 204 detects the respiratory sound of the subject, and the data storage device 112 stores the respiratory sound data. Typically, a time stamp is used to make respiration data correspond to respiratory sound data.

Figure 5:
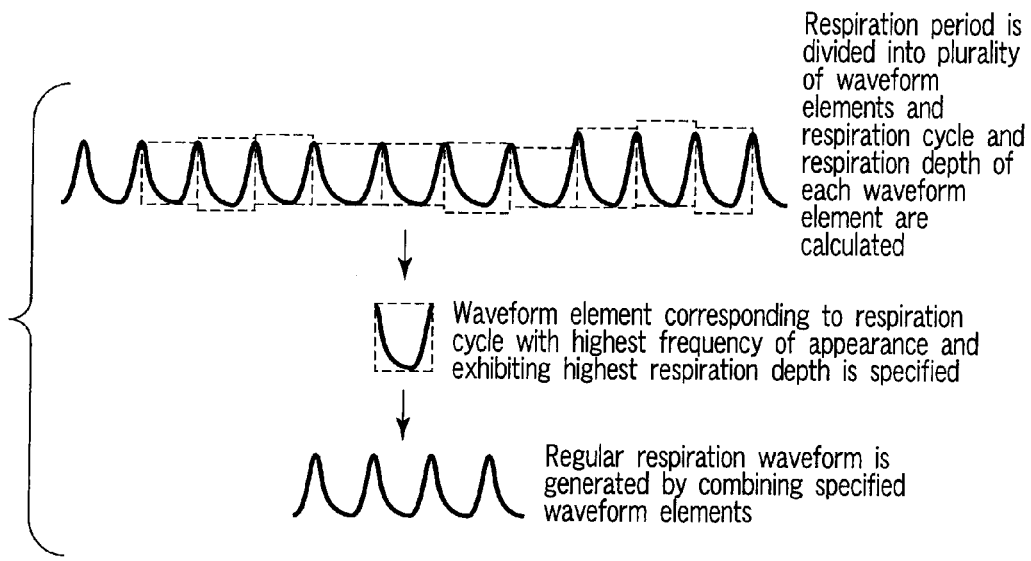
FIG. 5 is a chart showing a first method of generating a regular respiration waveform by a regular respiration waveform generating unit in FIG. 1.

FIG. 5 schematically shows a first procedure for generating a regular respiration waveform. The data storage device 112 supplies respiration data acquired by the breath detector 203 for at least a period of one min to the regular respiration waveform generating unit 207. First of all, the regular respiration waveform generating unit 207 specifies the end of an inspiration period from at least a respiration waveform corresponding to one min on the basis of the maximum value of the respiration waveform, and divides the entire respiration interval into a plurality of respiration periods. The respiration waveform is then divided into a plurality of waveform elements in accordance with the plurality of divided respiration periods. The regular respiration waveform generating unit 207 calculates the respiration motion cycle and respiration depth of each of a plurality of waveform elements. The unit then specifies a respiration cycle with the highest frequency of appearance among the calculated respiration cycles. The unit alternatively specifies waveform elements with the highest respiration depths among a plurality of respiration elements corresponding to the specified respiration cycle with the highest frequency of appearance. The unit generates a regular respiration waveform by combining the specified waveform elements. Obviously, this regular respiration waveform has a perfectly constant respiration cycle and respiration depth. This waveform shape corresponds to a breathing motion unique to the subject.

Figure 8:
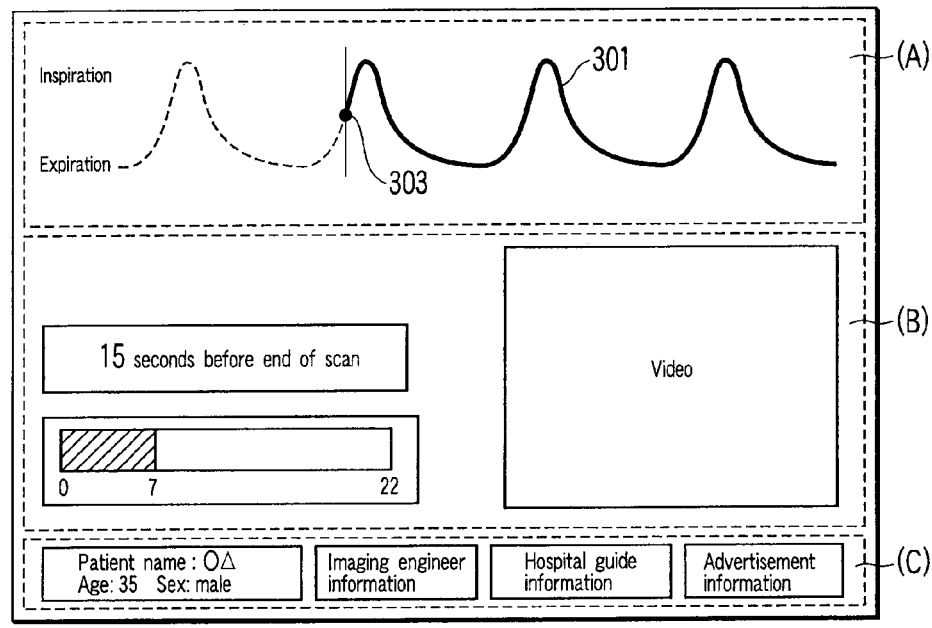
FIG. 8 is a view showing a display example of the gantry mount display in FIG. 1.

The display/loudspeaker control unit 205 forms a respiration guide window in accordance with the generated regular respiration waveform, and causes the gantry mount display 201 to display the window. FIG. 8 shows an example of a respiration guide window. Note that this window comprises a respiration guide display area (A), a display area (B) for providing instructions for the subject and various kinds of information associated with examination and the like, and a display area (C) aimed at both the subject and the operator. The display area (B) displays, as information corresponding to the progresses of examination and scan, information such as the remaining time of a scan, an examination time schedule, and the remaining rest time to a next scan which corresponds to the rest time between a scan and the next scan. The display area (C) displays, for example, patient information, imaging engineer information, hospital guide information, and advertisement information. Window construction in the areas (B) and (C) is performed by the control unit 205 or other constituent elements specialized for the respective areas.

In the respiration guide display area (A), a graphic pattern 301 of a regular respiration waveform is displayed as if it flowed from the right side to the left side with the lapse of the actual time. A respiration guide mark 303 is superimposed on the graphic pattern 301 of the regular respiration waveform. The horizontal position of the respiration guide mark 303 is fixed at a specific position within the window, and the vertical position of the respiration guide mark 303 vertically moves in accordance with the flow of the graphic pattern 301 of the regular respiration waveform. The subject can gradually stabilize his/her breathing motion by receiving guidance based on the vertical movement of the respiration guide mark 303 in accordance with the flow of the graphic pattern 301 of the regular respiration waveform.

The display/loudspeaker control unit 205 plays back respiratory sound recorded from the subject through the microphone 204 at the same time of the detection of the waveform elements in synchronism with the flow of the graphic pattern 301 of the regular respiration waveform and the vertical movement of the respiration guide mark 303, and the loudspeaker unit 202 outputs the sound. This respiratory sound is the one produced by the subject by himself/herself, and can further promote stabilizing the breathing motion in accordance with the flow of the graphic pattern 301 of the regular respiration waveform and the vertical movement of the respiration guide mark 303.

Figure 6:
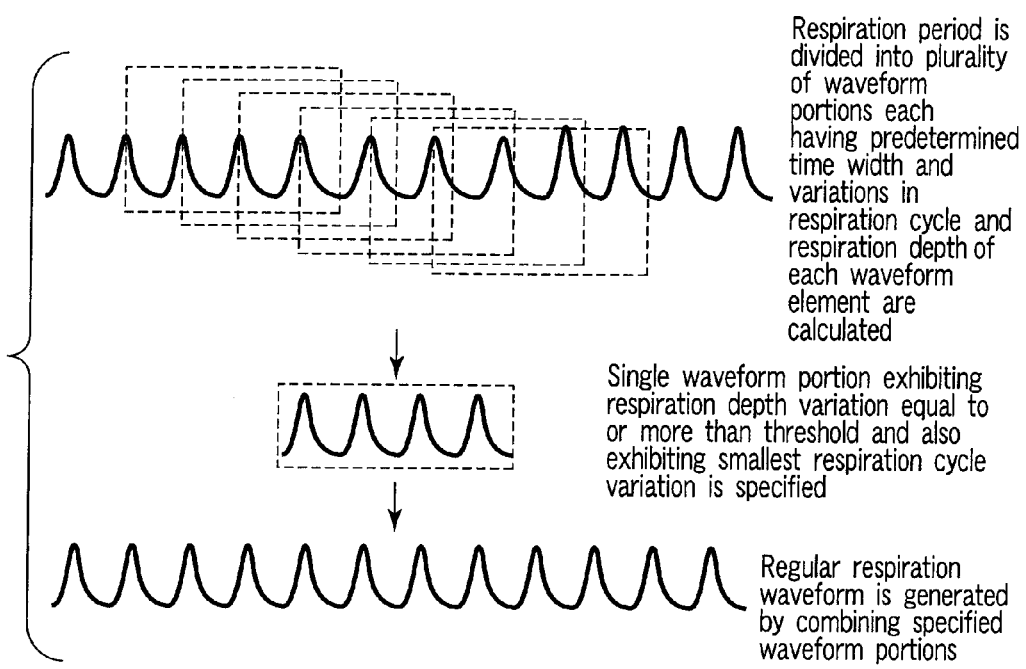
FIG. 6 is a chart showing a second method of generating a regular respiration waveform by the regular respiration waveform generating unit in FIG. 1.

FIG. 6 schematically shows a second procedure for generating a regular respiration waveform. As described above, the data storage device 112 supplies respiration data acquired by the breath detector 203 for at least a period of one min to the regular respiration waveform generating unit 207. First of all, the regular respiration waveform generating unit 207 specifies the end of an inspiration period from at least a respiration waveform corresponding to one min on the basis of the maximum value of the respiration waveform.

A window period is defined in an interval from the end of each specified inspiration period to the end of a predetermined fixed time. A window period can be arbitrarily adjusted by the operator, and is set to have a width large enough to include at least three respiration periods, typically five to ten sec. Variations in respiration cycle and respiration depth are calculated for each window period. A variation in respiration cycle is calculated as the difference between the longest respiration cycle and the shortest respiration cycle among a plurality of respiration periods included in a window period. A variation in respiration depth is calculated as the difference between the largest respiration depth and the smallest respiration depth in a plurality of respiration periods included in a window period.

The regular respiration waveform generating unit 207 narrows down a plurality of waveform portions corresponding to a plurality of window periods into a plurality of waveform portions exhibiting respiration depths equal to or more than a given depth, i.e., a given threshold, and specifies a waveform portion exhibiting the smallest variation in respiration cycle. Note that if there are a plurality of waveform portions exhibiting the smallest variation respiration cycle, a waveform portion exhibiting the largest respiration depth is selected.

This specified waveform portion represents the stablest breathing motion exhibiting a sufficiently large respiration depth and repetition of respiration in a predetermined cycle. The specified waveform portions are combined to generate a regular respiration waveform. As shown in FIG. 8, a respiration guide window is displayed on the gantry mount display 201 under the control of the display/loudspeaker control unit 205 in accordance with this regular respiration waveform, as shown in FIG. 8. In addition, the respiratory sound recorded from the subject through the microphone 204 at the same time as the detection of the waveform portions is played back and output from the loudspeaker unit 202 in synchronism with the flow of the graphic pattern 301 of the regular respiration waveform and the vertical movement of the respiration guide mark 303.

Figure 7:
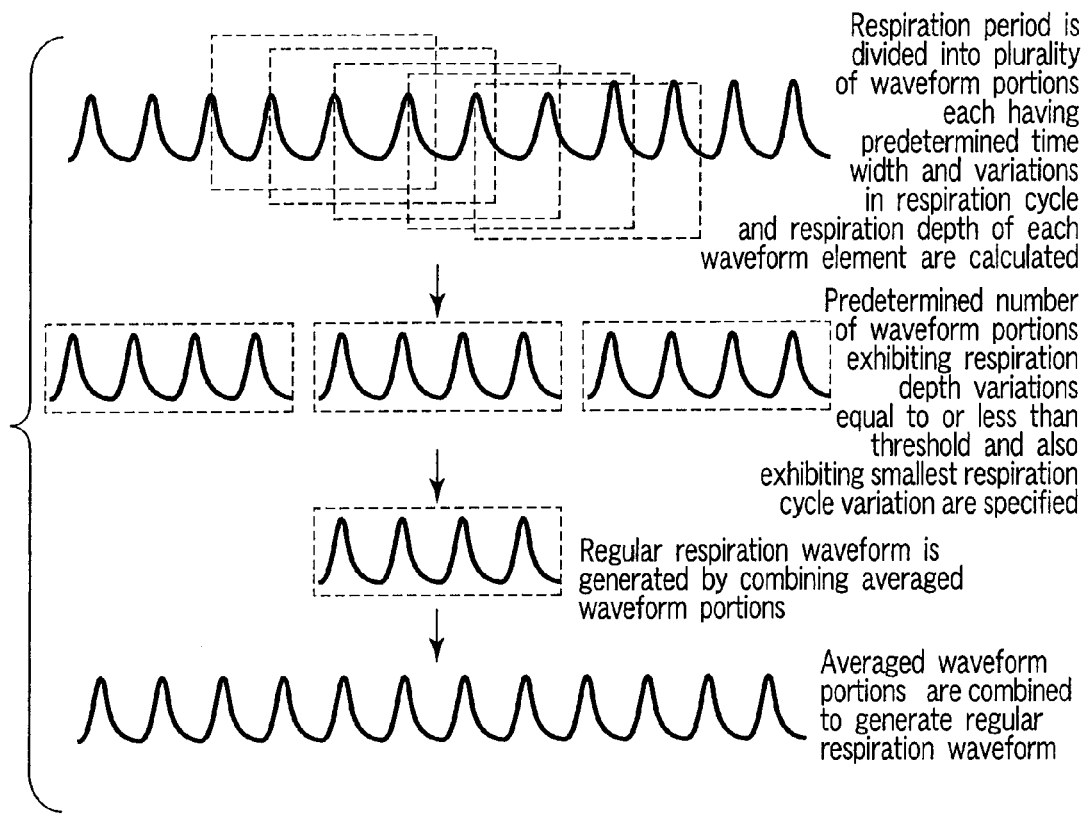
FIG. 7 is a chart showing a third method of generating a regular respiration waveform by the regular respiration waveform generating unit in FIG. 1.

FIG. 7 schematically shows a third procedure for generating a regular respiration waveform. As in the above case, the data storage device 112 supplies respiration data acquired by the breath detector 203 for at least a period of one min to the regular respiration waveform generating unit 207. First of all, the regular respiration waveform generating unit 207 specifies the end of an inspiration period from at least a respiration waveform corresponding to one min on the basis of the maximum value of the respiration waveform. A window period is defined in an interval from the end of each specified inspiration period to the end of a predetermined fixed time. A window period includes at least three respiration periods. Variations in respiration cycle and respiration depth are calculated for each window period. A variation in respiration cycle is calculated as the difference between the longest respiration cycle and the shortest respiration cycle among a plurality of respiration periods included in a window period. A variation in respiration depth is calculated as the difference between the largest respiration depth and the smallest respiration depth in a plurality of respiration periods included in a window period.

The regular respiration waveform generating unit 207 narrows down a plurality of waveform portions corresponding to a plurality of window periods into a plurality of waveform portions exhibiting respiration depths equal to or more than a given threshold, and specifies, among the waveform portions, a predetermined number of waveform portions in order of increasing variations in respiration cycle, e.g., top three waveform portions in order of increasing variations in respiration cycle.

The regular respiration waveform generating unit 207 averages these three specified waveform portions to generate a single specified waveform portion. In averaging these waveform portions, the unit extracts three respiration index values in the same time phase from the three waveform portions and calculates the average value of the index values. That is, the average waveform portion represents a temporal change in the average of the three respiration index values.

Note that a processing method of generating a single waveform portion from three waveform portions is not limited to averaging processing, and it suffices to, for example, generate a single waveform portion from the median of three respiration index values in the respective time phases of three waveform portions or generate a single waveform portion from the maximum or minimum value of three respiration index values.

The generated average waveform portions are combined to generate a regular respiration waveform. As shown in FIG. 8, a respiration guide window is displayed on the gantry mount display 201 in accordance with this regular respiration waveform under the control of the display/loudspeaker control unit 205. In addition, respiratory sound recorded from the subject through the microphone 204 at the same time as the detection of any of the three waveform portions is played back and output from the loudspeaker unit 202 in synchronism with the flow of the graphic pattern 301 of the regular respiration waveform and the vertical movement of the respiration guide mark 303. Typically, respiratory sound is played back upon detection of a waveform portion whose variation in respiration cycle indicates the median of variations in respiration cycle when a waveform portion exhibiting the smallest variation in respiration cycle and a waveform portion exhibiting the largest variation in respiration cycle are excluded from the three waveform portions.

As described above, this embodiment has the special effect of promoting stabilizing the breathing motion of a subject by presenting, as a respiration guide, a unique respiration waveform which the subject has produced by himself/herself in a period during which he/she stably repeats breathing and by playing back the corresponding actual respiration sound.

Second Embodiment

An embodiment of an X-ray computed tomographic apparatus according to the present invention will be described below with reference to the views of the accompanying drawing. Note that the present invention is not limited to an X-ray computed tomographic apparatus and can be applied to other medical imaging apparatuses which generate images associated with a subject to be examined, e.g., an X-ray diagnostic apparatus, magnetic resonance imaging apparatus (MRI), ultrasonic diagnostic apparatus, and gamma camera. The present invention can also be applied to an electrocardiographic information display apparatus specialized as an electrocardiographic information display function. An X-ray computed tomographic apparatus will be exemplified below. Note that X-ray computed tomographic apparatuses include various types of apparatuses, e.g., a rotate/rotate-type apparatus in which an X-ray tube and an X-ray detector rotate together around a subject to be examined, and a stationary/rotate-type apparatus in which many detection elements are arrayed in the form of a ring, and only an X-ray tube rotates around a subject to be examined. The present invention can be applied to either type. In order to reconstruct one-slice tomogram data, projection data corresponding to one rotation around a subject to be examined, i.e., about 360°, is required, or (180°+view angle) projection data is required in the half scan method. The present invention can be applied to either of these reconstruction schemes. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. As an X-ray detection element, either of these schemes can be used. Recently, with advances toward the commercialization of a so-called multi-tube type X-ray computed tomographic apparatus having a plurality of pairs of X-ray tubes and X-ray detectors mounted on a rotating ring, related techniques have been developed. The present invention can be applied to both a conventional single-tube type X-ray computed tomographic apparatus and a multi-tube type X-ray computed tomographic apparatus. The single-tube type X-ray computed tomographic apparatus will be exemplified here.

Figure 9:
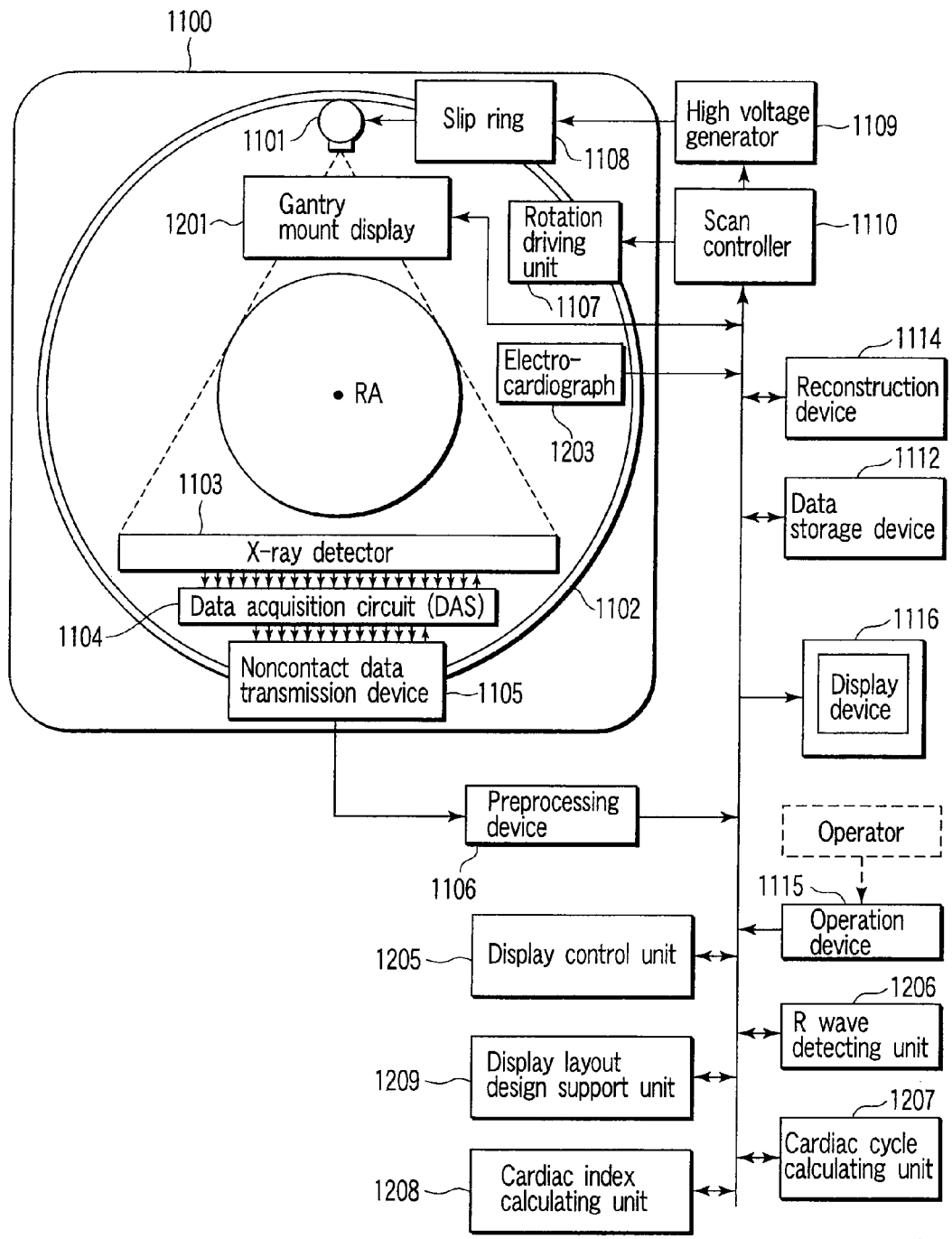
FIG. 9 is a block diagram showing the arrangement of an X-ray computed tomographic apparatus according to another embodiment of the present invention.

FIG. 9 shows the arrangement of the main part of an X-ray computed tomographic apparatus according to this embodiment. The X-ray computed tomographic apparatus according to this embodiment includes a gantry 1100. The gantry 1100 includes an annular rotating frame 1102. A rotation driving unit 1107 drives/rotates the rotating frame 1102 about a rotation axis RA. An X-ray tube 1101 and an X-ray detector 1103 are mounted on the rotating frame 1102. The X-ray tube 1101 faces the X-ray detector 1103 through the rotation axis RA. The X-ray tube 1101 receives a tube voltage and filament current from a high voltage generator 1109 through a slip ring 1108, and generates X-rays. The X-ray detector 1103 detects X-rays transmitted through the subject and outputs an electrical signal reflecting the dose of incident X-rays. A preprocessing device 1106 receives a signal output from the X-ray detector 1103 through a data acquisition circuit 1104 and a noncontact data transmission device 1105. The data output from the data acquisition circuit 1104 is generally called pure raw data. The preprocessing device 1106 performs preprocessing such as sensitivity correction and logarithmic transformation for the pure raw data. The preprocessed pure raw data is data at a stage immediately before reconstruction processing, and is generally called projection data or raw data. A data storage device 1112 stores the projection data.

An electrocardiograph 1203 is placed on or near the gantry 1100. The electrocardiograph 1203 detects an electrical phenomenon accompanying the cardiac pulsation of the subject, and generates electrocardiographic data as a temporal change in the phenomenon. The electrocardiographic data is supplied to an R wave detecting unit 1206 (to be described later) as well as the data storage device 1112.

Figure 10:
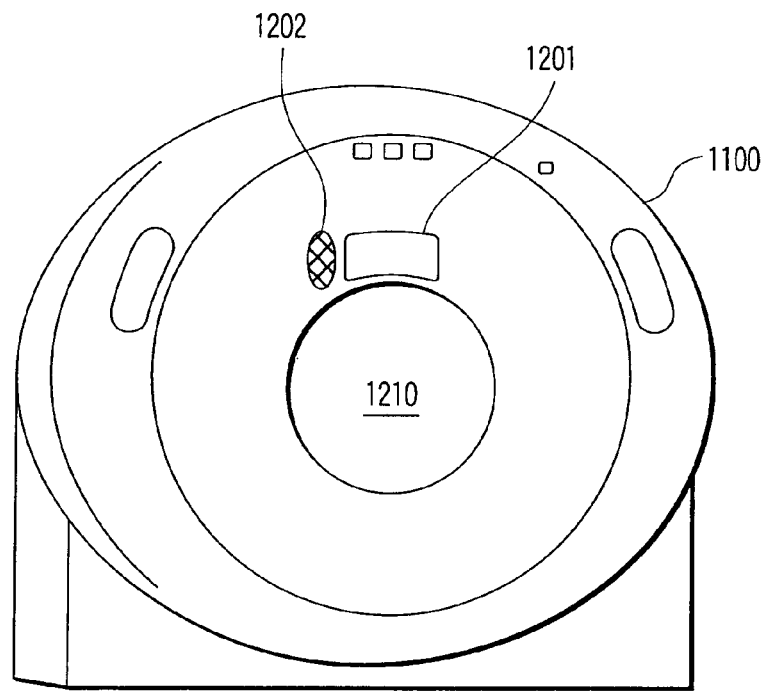
FIG. 10 is a view showing the mount position of a gantry mount display in FIG. 9 on a gantry.
Figure 11:
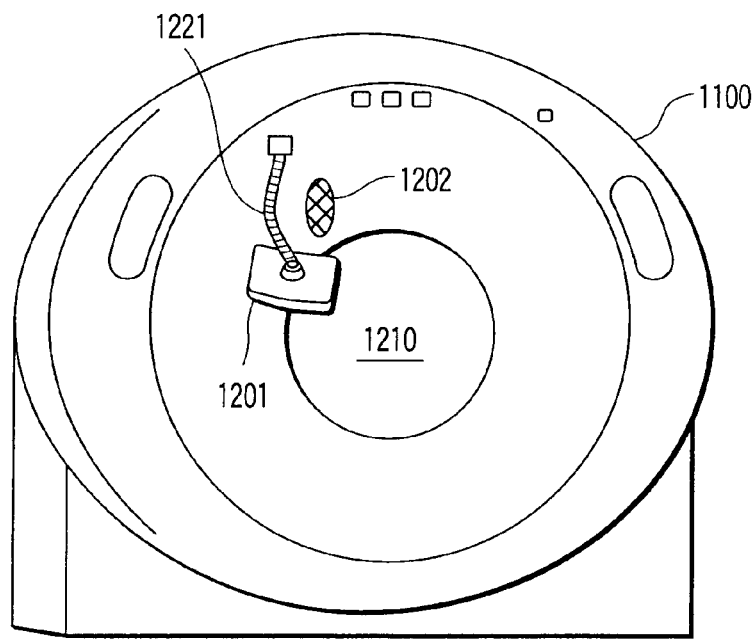
FIG. 11 is a view showing another example of the mount position of the gantry mount display in FIG. 9 on the gantry.

A gantry mount display 1201 is placed on or near the gantry 1100. More specifically, as shown in FIG. 10, the gantry mount display 1201 comprising a liquid crystal panel and the like is placed on the housing surface of the gantry 100 at a position where the display does not become an X-ray blockage and can be visually recognized by the subject inserted into an opening portion 1210 and the operator who stands near the gantry 1100, typically a cone-shaped portion around the opening portion 1208. As shown in FIG. 11, the gantry mount display 1201 may be suspended from the gantry 1100 through an articulated arm 1221.

A scan controller 1110 controls the operations of the rotation driving unit 1107, high voltage generator 1109, and the like to perform data acquisition (scanning). A reconstruction device 1114 reconstructs tomogram data on the basis of projection data stored in the data storage device 1112. A display device 1116 is provided to display mainly tomogram data. An operation device 1115 comprises an operation unit which includes a keyboard, mouse, and the like and is used to input operator instructions, and a display unit for displaying an operation window.

A display control unit 1205 is provided to perform processing and control required to lay out display items such as the cardiac index calculated by a cardiac index calculating unit 1208 and an electrocardiogram in accordance with the display layout designed by the operator through the operation device 1115 under the support of a display layout design support unit 1209 and to display the laid-out display items on the gantry mount display 1201. The R wave detecting unit 1206 detects a characteristic wave of the electrocardiogram supplied from the electrocardiograph 1203, typically an R wave. A cardiac cycle calculating unit 1207 calculates the period of the R wave detected by the R wave detecting unit 1206, i.e., a cardiac cycle. The cardiac index calculating unit 1208 calculates a plurality of cardiac indexes associated with the heartbeat state of the subject on the basis of the cardiac cycle calculated by the cardiac cycle calculating unit 1207.

The following are examples of the plurality of cardiac indexes which can be calculated by the cardiac index calculating unit 1208:

heart rate: the number of heartbeats per min, which is calculated for each cardiac cycle as the value obtained by dividing 60 sec by a cardiac cycle as the time (unit=sec) required for one heartbeat.

interval average heart rate: the average value of a plurality of heart rates repeatedly calculated for every R wave detection (cardiac cycle calculation) at predetermined intervals, e.g., intervals of 10 sec.

heart rate difference: the value calculated by subtracting a heart rate from an interval average heart rate as a value representing a variation in heart rate corresponding to the interval average heart rate.

value calculated by free formula: the value calculated by a formula arbitrarily set with a heart rate, cardiac cycle, interval average heart rate, heart rate difference, and the like as variables.

The display layout design support unit 1209 performs processing for a window and associated processing. This window supports the operator to designate at least one display item, of a plurality of display items which can be displayed, which is to be actually displayed, and to design a display layout indicating how the designated display items are arranged in the display area. Display items include the electrocardiographic waveform generated by the electrocardiograph 1203, a heart rate history, and a heart rate difference history in addition to the heart rate, interval average heart rate, heart rate difference, and free calculation value which are generated by the cardiac index calculating unit 1208. A heart rate history is, for example, a latest list of heart rates corresponding to 10 heartbeats which are directly written in numeric form in chronological order. A heart rate difference history is a latest list of heart rate differences corresponding to 10 heartbeats which are directly written in numeric form in chronological order.

Figure 12:
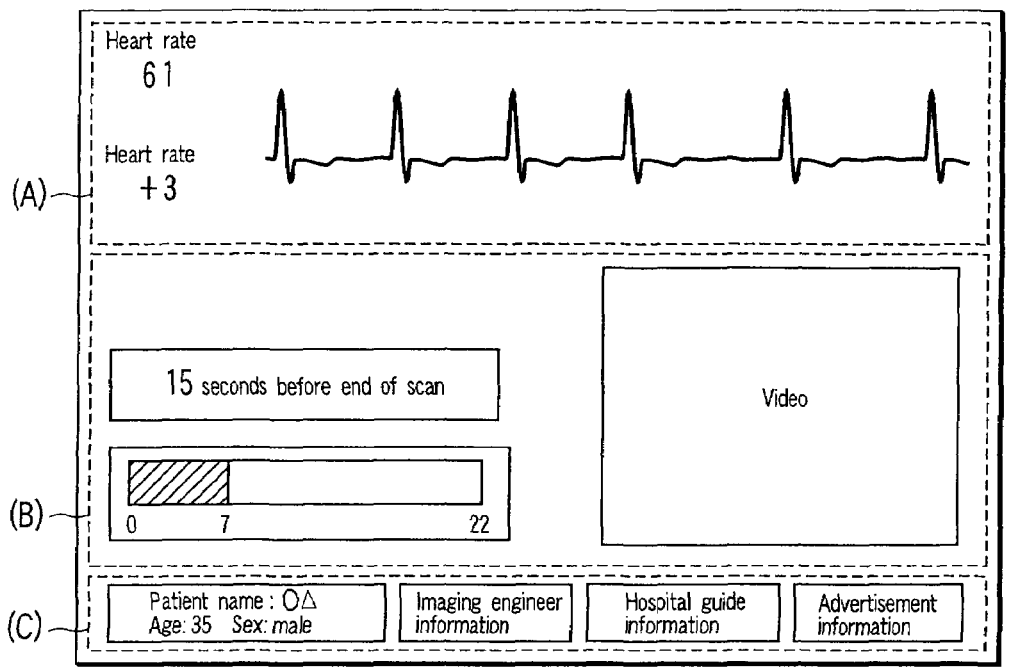
FIG. 12 is a view showing a display example of the gantry mount display in FIG. 9.

FIG. 12 shows a display window example which is displayed on the gantry mount display 1201 under the control of the display control unit 1205. In the example shown in FIG. 12, a heart rate, heart rate difference, and electrocardiographic waveform are laid out as display items in an electrocardiographic information area (A). Note that this window comprises a display area (B) for providing various kinds of information associated with instructions, examination, and the like for the subject and a display area (C) aimed at both the subject and the operator, in addition to the electrocardiographic information area (A). The display area (B) displays, as information corresponding to the progresses of examination and scan, for example, the remaining time of a scan, an examination time schedule, the remaining rest time to a next scan which corresponds to the rest time between the current scan and the next scan. The display area (C) displays, for example, patient information, imaging engineer information, hospital guide information, and advertisement information. Window construction in the areas (B) and (C) is performed by the display/loudspeaker control unit 1205 or other constituent elements specialized for the respective areas.

The following is actual operation for displaying electrocardiographic information. The electrocardiograph 1203 sequentially detects electrocardiograms associated with the subject in real time. The R wave detecting unit 1206 and the cardiac cycle calculating unit 1207 sequentially execute R wave detection processing and cardiac cycle calculation processing, respectively, in real time on the basis of the electrocardiograms detected in real time. Along with this operation, the cardiac index calculating unit 1208 sequentially calculates a plurality of cardiac indexes in real time, which are immediately reflected in the display on the gantry mount display 1201. That is, the electrocardiogram displayed on the gantry mount display 1201 and the electrocardiographic index reflect the current heartbeat state of the subject. This allows the operator to comprehend the operation state of the electrocardiograph itself and the current heartbeat state of the subject. In addition, the operator can objectively determine from the electrocardiographic index whether the heartbeat motion is stable. Such real-time display of electrocardiographic information is started before scanning (data acquisition). The operator then can start scanning operation accompanying actual generation of X-rays by observing the electrocardiographic information and pressing a scan trigger button when the heartbeat becomes stable to some degree.

Figure 13:
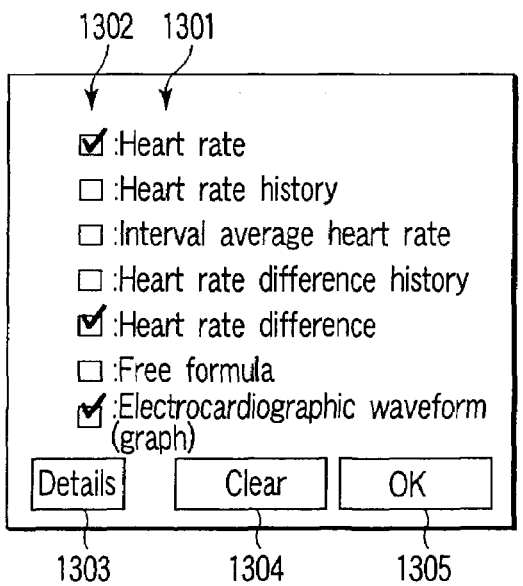
FIG. 13 is a view showing a display item designation window example provided by a display layout support unit in FIG. 9.

FIG. 13 shows a simple display item designation window provided by the display layout design support unit 1209. This window is displayed on the display unit of an operation device 1115 when the operator performs specific operation through the operation device 1115 to start the display layout design support function. This window displays a list of names 1301 of the plurality of display items described above together with check boxes 1302. When the operator checks one or a plurality of display items which he/she wants to display and clicks the "OK" button, the display control unit 1205 lays out the checked display items in accordance with default positions and displays them on the gantry mount display 1201. Clicking a "clear" button 1304 will cancel all the checks. Clicking a "details" button 1303 will cause the display layout design support unit 1209 to display the detailed display layout design window shown in FIG. 14 on the display unit of the operation device 1115.

The detailed layout design window shown in FIG. 14 includes a virtual display area 1401 corresponding to the display area (A) of the gantry mount display 201. Boxes 1402 to 1408 indicating display items are displayed below the virtual display area 1401. The size ratios of the boxes 1402 to 1408 to the virtual display area 1401 correspond to the ratios of the display ranges of the respective display items to the display area (A) of the gantry mount display 1201. As shown in FIG. 15, the operator operates the operation unit of the operation device 1115 to drag and drop at least one of the boxes 1402 to 1408 which corresponds to a display item which the operator wants to display from the display item list to a position in the virtual display area 1401 which the operator wants to display the display item. This operation makes it possible to complete designation of a display item which the operator wants to display and design of a display layout. Returning a box from the virtual display area 1401 to the display item list will cancel the display designation. All cancellations are made by clicking a "clear" button 1409. When the operator clicks the "OK" button 1410, the display control unit 1205 displays the display items on the gantry mount display 1201 in accordance with the designed layout.

As described above, according to this embodiment, since the latest electrocardiographic information such as a cardiac index and an electrocardiogram is always displayed on the gantry mount display 1201, the operator can objectively comprehend the operation state of the electrocardiograph itself and the current heartbeat state of the subject. This makes it possible to properly measure the timing of pressing the scan trigger button.

Third Embodiment

An embodiment of a medical imaging apparatus according to the present invention will be described below with reference to the views of the accompanying drawing. Note that medical imaging apparatuses which generate images associated with a subject to be examined include an X-ray diagnostic apparatus, X-ray computed tomographic apparatus (X-ray CT apparatus), magnetic resonance imaging apparatus (MRI), ultrasonic diagnostic apparatus, gamma camera, and the like. In this case, an X-ray computed tomographic apparatus will be exemplified as a medical imaging apparatus. X-ray computed tomographic apparatuses include various types of apparatuses, e.g., a rotate/rotate-type apparatus in which an X-ray tube and X-ray detector rotate together around a subject to be examined, and a stationary/rotate-type apparatus in which many detection elements are arrayed in the form of a ring, and only an X-ray tube rotates around a subject to be examined. The present invention can be applied to either type. In this case, the rotate/rotate type, which is currently the mainstream, will be exemplified. In order to reconstruct one-slice tomogram data, projection data corresponding to one rotation around a subject to be examined, i.e., about 360°, is required, or (180°+view angle) projection data is required in the half scan method. The present invention can be applied to either of these reconstruction schemes. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. As an X-ray detection element, either of these schemes can be used. In this case, the former type, i.e., the indirect conversion type, will be exemplified. Recently, with advances toward the commercialization of a so-called multi-tube type X-ray computed tomographic apparatus having a plurality of pairs of X-ray tubes and X-ray detectors mounted on a rotating ring, related techniques have been developed. The present invention can be applied to both a conventional single-tube type X-ray computed tomographic apparatus and a multi-tube type X-ray computed tomographic apparatus. The single-tube type X-ray computed tomographic apparatus will be exemplified here.

Figure 16:
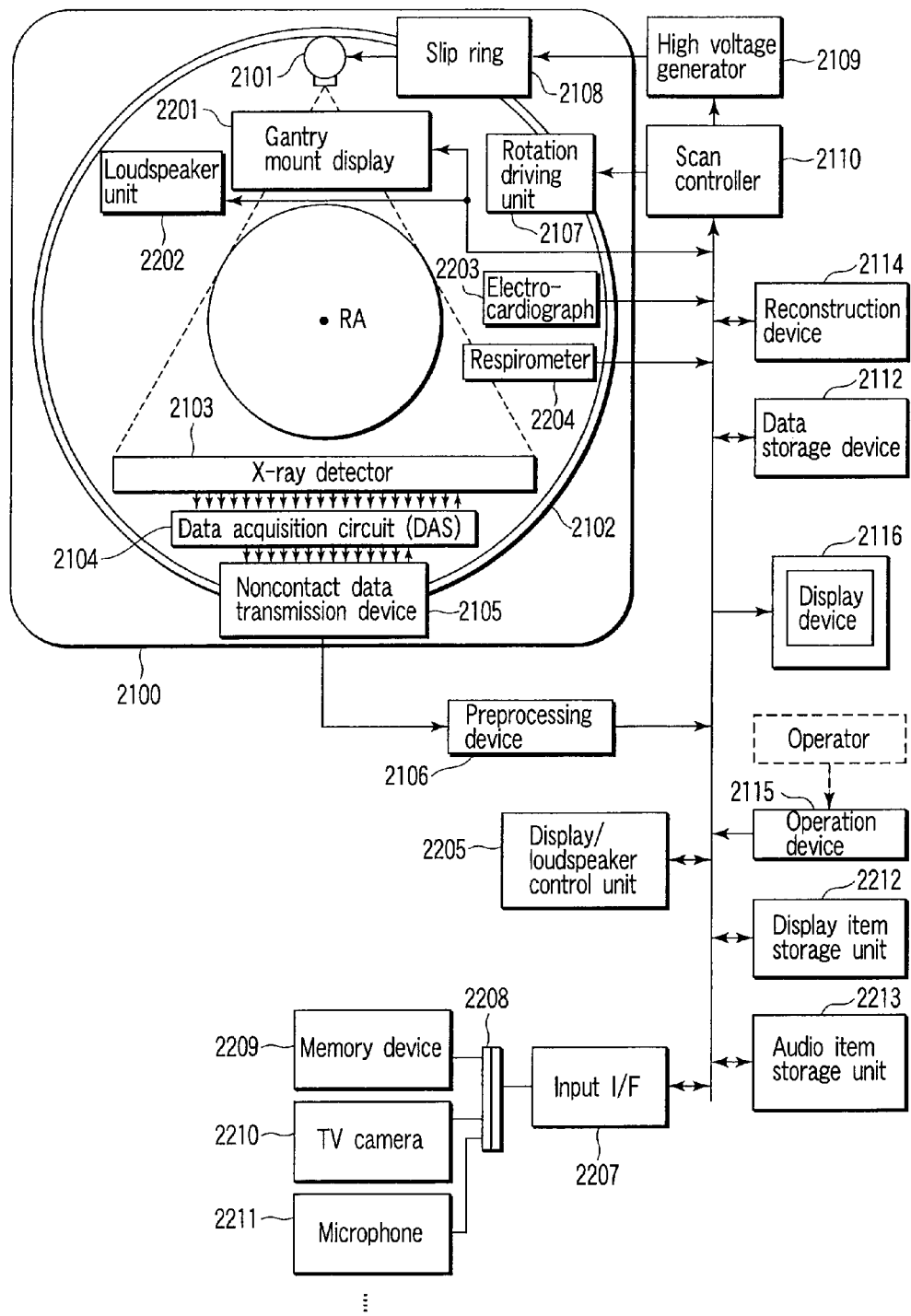
FIG. 16 is a block diagram showing the arrangement of an X-ray computed tomographic apparatus according to still another embodiment of the present invention.

FIG. 16 shows the arrangement of the main part of an X-ray computed tomographic apparatus according to this embodiment. The X-ray computed tomographic apparatus according to this embodiment includes a gantry 2100. The gantry 2100 includes an annular rotating frame 2102. A rotation driving unit 2107 drives/rotates the rotating frame 2102 about a rotation axis RA. An X-ray tube 2101 and an X-ray detector 2103 are mounted on the rotating frame 2102 so as to face each other. The X-ray tube 2101 receives a tube voltage and filament current from a high voltage generator 2109 through a slip ring 2108, and generates X-rays. The X-ray detector 2103 detects X-rays transmitted through the subject and outputs an electrical signal reflecting the dose of incident X-rays. A preprocessing device 2106 receives a signal (pure raw data) output from the X-ray detector 2103 through a data acquisition circuit 2104 and a noncontact data transmission device 2105. In the preprocessing device 2106, a data storage device 2112 stores data having undergone sensitivity correction, logarithmic transformation, and the like (called projection data or raw data). An electrocardiograph 2203 and a respirometer 2204 are provided on or apart from the gantry 2100.

Figure 17:
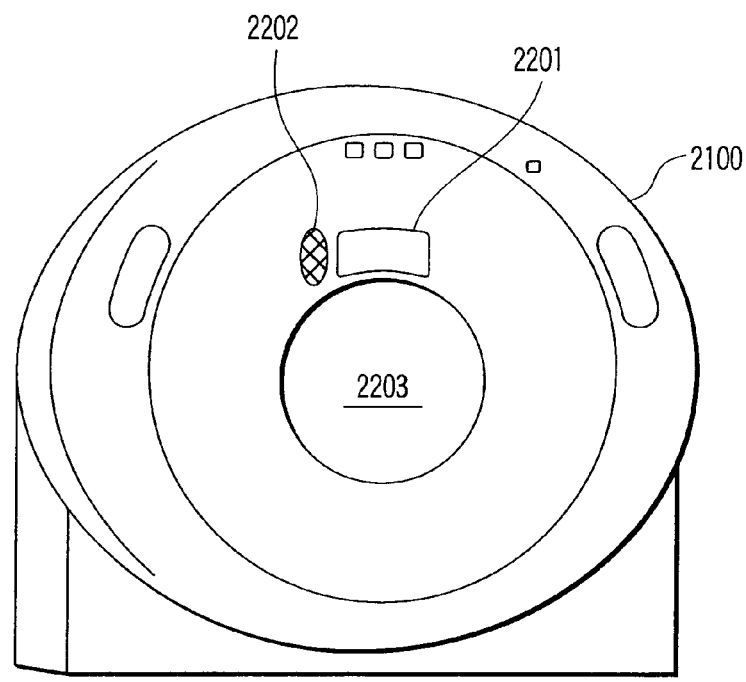
FIG. 17 is a view showing an example of a gantry and a display mounted thereon.
Figure 18:
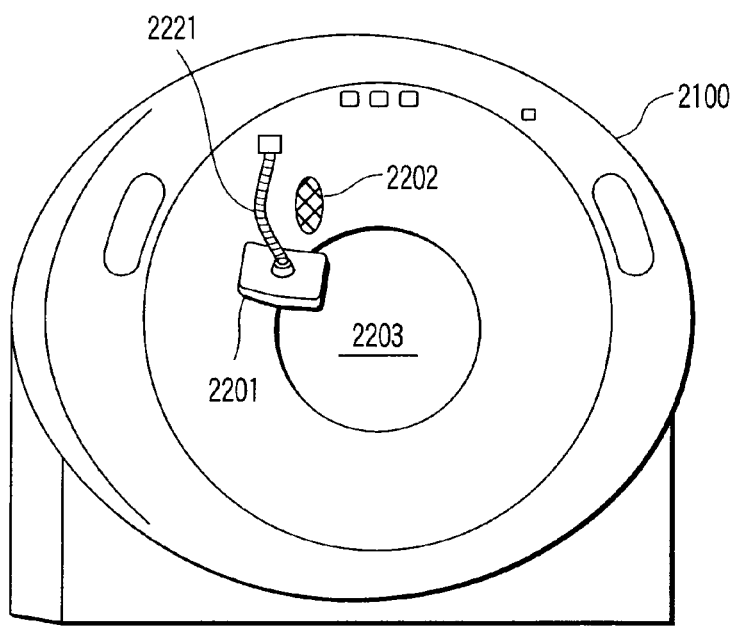
FIG. 18 is a view showing another example of the gantry and the display mounted thereon.

A gantry mount display 2201 is placed on or near the gantry 2100. More specifically, as shown in FIG. 17, the gantry mount display 2201 comprising a liquid crystal panel and the like is placed on the housing surface of the gantry 2100 at a position where the display does not become an X-ray blockage and can be visually recognized by the subject inserted into an opening portion 2203, typically a cone-shaped portion around the opening portion 2203. As shown in FIG. 18, the gantry mount display 2201 may be suspended from the gantry 2100 through an articulated arm 2221. A gantry loudspeaker unit 2202 is placed on or near the gantry 2100. More specifically, the gantry loudspeaker unit 2202 is placed on the housing surface of the gantry 2100 at a position where the loudspeaker unit does not become an X-ray blockage and the subject inserted in the opening portion 2203 can easily hear, typically a cone-shaped portion around the opening portion 2203.

A scan controller 2110 controls the operations of the rotation driving unit 2107, high voltage generator 2109, and the like to perform data acquisition (scanning). A reconstruction device 2114 reconstructs tomogram data on the basis of projection data stored in the data storage device 2112. The display device 2116 is provided to display mainly tomogram data. An operation device 2115 comprises a keyboard, mouse, and the like and is used to input operator instructions.

A display/loudspeaker control unit 2205 controls the display of the gantry mount display 2201 and the audio output (voice output) of the gantry loudspeaker unit 2202. This embodiment is characterized by the display of the gantry mount display 2201 and the audio output of the gantry loudspeaker unit 2202.

An audio item storage unit 2213 stores a plurality of audio files (voice files) associated with spoken instructions to a subject, which are ordered in accordance with the progress of examination. Audio files are associated with a plurality of examination stages representing the progresses of examination and scan. For example, an audio file of the message "hold your breath" to be played back at the time of breath holding imaging is prepared. The audio item storage unit 2213 stores a plurality of audio files associated with a music (an ambient music, healing music, or the like) having a relaxing effect regardless of an examination instruction and the like, a reading, a soft narration, and the like. These audio files of musical pieces having relaxing effects and the like are associated with a relaxing period after the end of breath holding and the rest time between scans.

The display/loudspeaker control unit 2205 selectively reads out an audio file from the audio item storage unit 2213 in accordance with a control signal representing an examination stage from the scan controller 2110. The loudspeaker unit 2202 then plays back the audio file.

Figure 20:
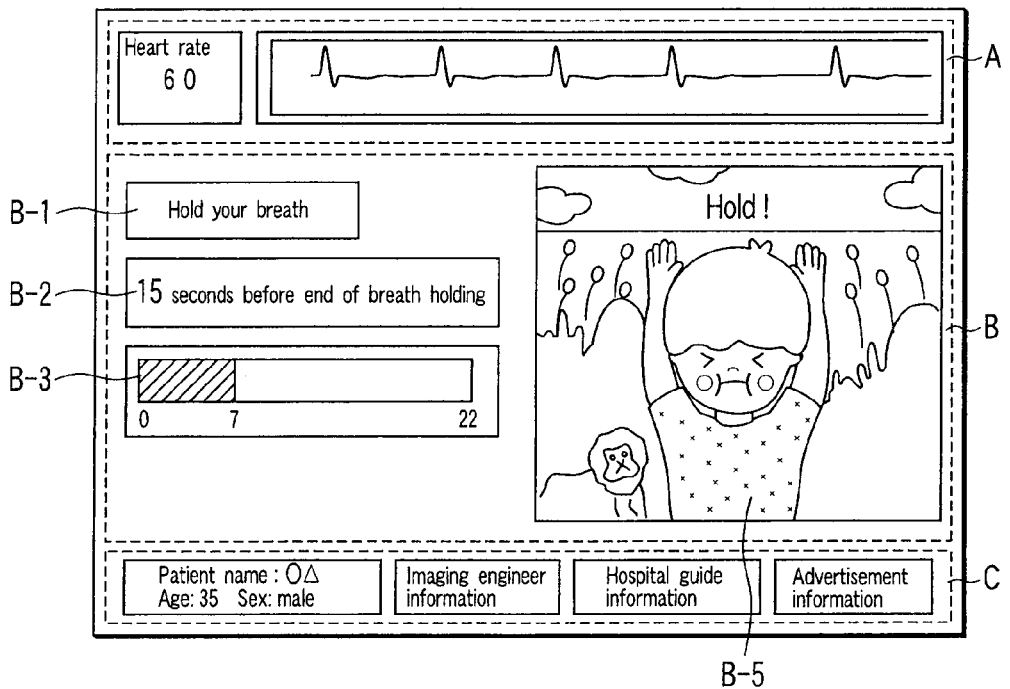
FIG. 20 is a view showing another example of the display window on the gantry mount display comprising the display window forming unit in FIG. 16.
Figures 21, 22, 23, 24:
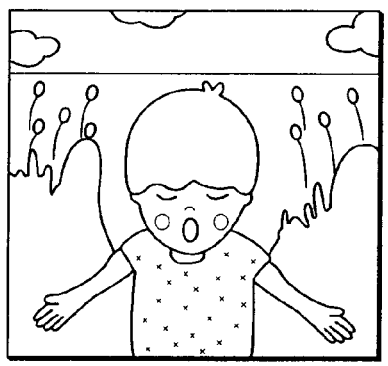
FIG. 21 is a view showing an example of a display item stored in a display item storage unit in FIG. 16.
FIG. 22 is a view showing another example of the display item stored in the display item storage unit in FIG. 16.
FIG. 23 is a view showing still another example of the display item stored in the display item storage unit in FIG. 16.
FIG. 24 is a view showing still another example of the display item stored in the display item storage unit in FIG. 16.

A display item storage unit 2212 stores a plurality of image files associated with still images or moving images. At least one or a plurality of image files are associated with the respective audio files stored in the audio item storage unit 2213. The display/loudspeaker control unit 2205 reads out, from the display item storage unit 2212, at least one image file which is read out from the audio item storage unit 2213 in accordance with a control signal representing an examination stage from the scan controller 2110 and is associated with an audio file to be played back, and causes the gantry mount display 2201 to display the image file. Ages and sexes may be associated with image files. In this case, among image files of the same kind, the image file of a preferred graphic pattern corresponding to an age and sex can be selectively displayed. For example, it is possible to display an image for an infant, as shown in FIG. 20.

A manager can perform various updating operations through the operation device 2115, e.g., storing a new audio file in the display item storage unit 2212, deleting an unnecessary audio file, and changing the association of an audio file with an examination stage. Likewise, the manager can perform various updating operations through the operation device 2115, e.g., storing a new image file in the display item storage unit 2212, deleting an unnecessary image file, and changing the association of an image file with an audio file. A storage management unit (not shown) updates the storage unit 2212 and 2213 in accordance with these updating operations.

Image files include character message files (FIGS. 21, 22, 24, 26, 28, 29, 38, 39, and 41) expressing a spoken instruction to the subject, the progress of a scan, the progress of examination, and the like in character messages. For Example, there are prepared text message files indicating the time to the start of breath holding, the remaining time to the end of breath holding, an instruction to stop breath holding, the time to the start of a scan, a state indicating that a scan is being performed, the remaining time to the end of a scan, and the like. Even if the subject fails to listen to a spoken instruction or cannot easily understand it by voice, the subject can visually recognize the instruction or can sequentially visually recognize the contents of the current instruction.

Figure 40:
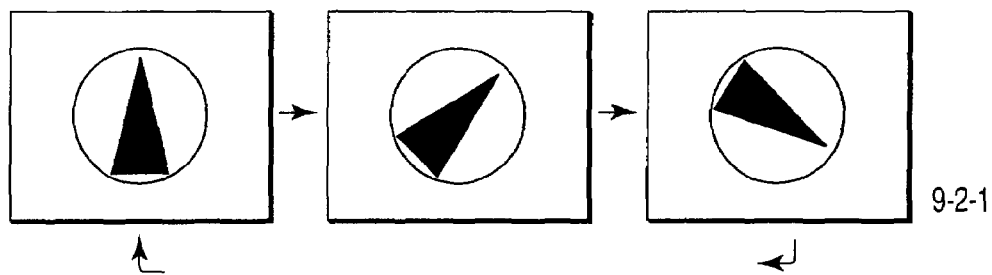
FIG. 40 is a view showing still another example of the display item stored in the display item storage unit in FIG. 16.
Figure 41:
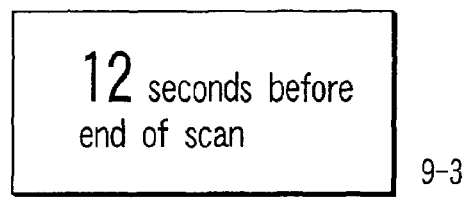
FIG. 41 is a view showing still another example of the display item stored in the display item storage unit in FIG. 16.
Figure 42:
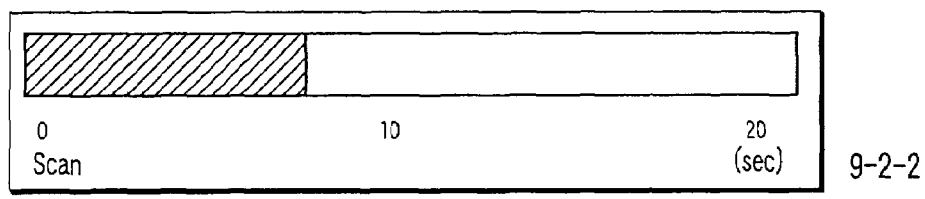
FIG. 42 is a view showing still another example of the display item stored in the display item storage unit in FIG. 16.

In addition, image files include graphic pattern message files (FIGS. 23, 25, 27, 30, 31, 40, and 42) for supplementing the contents of instructions by voice and text by using graphic patterns. For example, graphic pattern message files include the file of a graphic pattern indicating how the subject breathes deeply and the file of a graphic pattern indicating how the subject holds a breath. In addition, graphic pattern message files include the file of a graphic pattern indicating the ratio of the remaining time of breath holding to the entire time of breach holding, typically a bar graph (FIG. 27), the file of a graphic pattern indicating the ratio of the remaining time to the examination time, typically a bar graph (FIG. 30), the file of a graphic pattern indicating an examination time schedule together with the current time point, typically a bar graph (FIG. 31), the file of a moving image schematically expressing how the X-ray tube is rotating (FIG. 40), the file of a graphic pattern indicating the ratio of the remaining time to the entire scan time, typically a bar graph (FIG. 42), the file of a graphic pattern indicating the ratio of the remaining rest time to the next scan to the rest time between the current scan and the next scan, typically a bar graph, and the like.

Figure 43A:
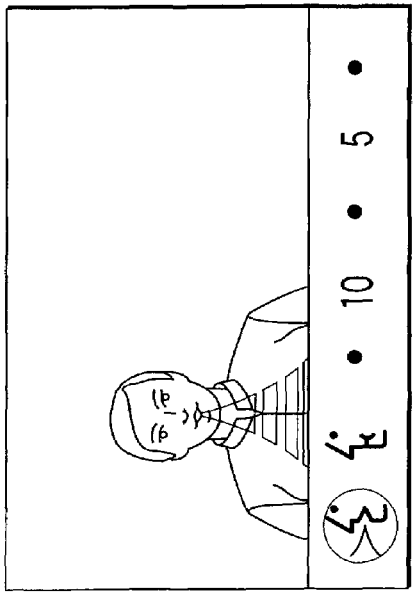
FIGS. 43A, 43B, 43C, and 43D are views each showing an example of a breath holding instruction image (guidance image)
Figure 43B:
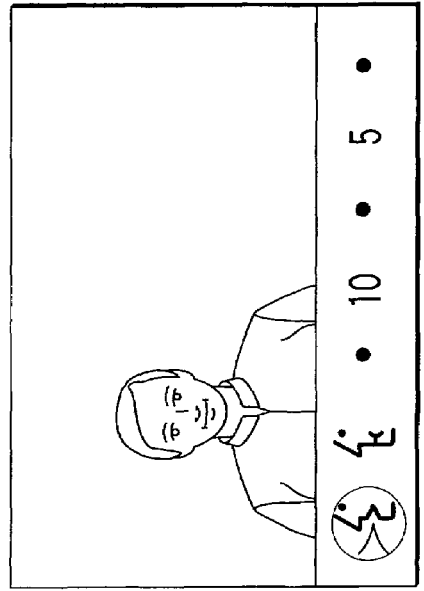
Figure 43C:
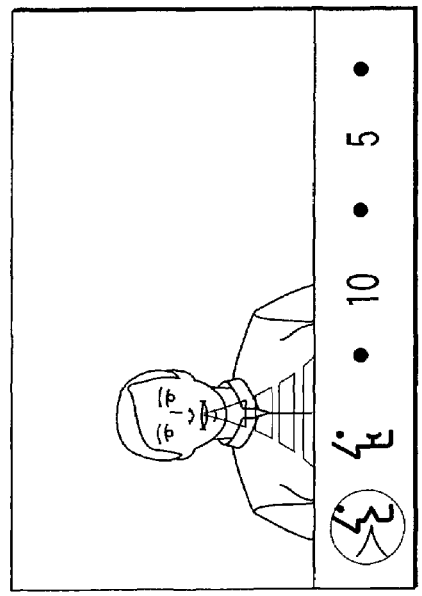
Figure 43D:
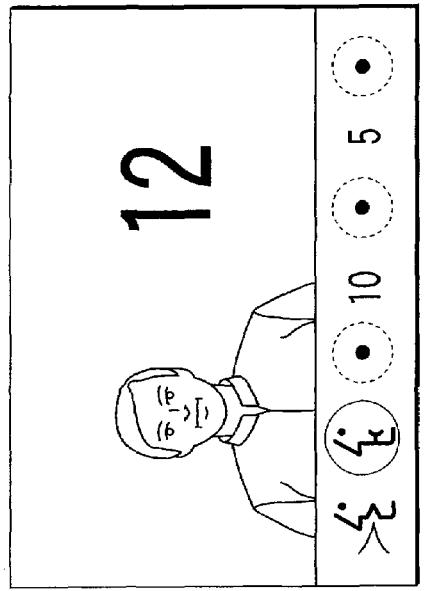

FIGS. 43A, 43B, 43C, and 43D each also show an example of a breath holding instruction image (guidance image). FIG. 43A shows a real image of a woman in her initial state of taking a deep breath. FIG. 43B shows a real image of the woman in a state of maintaining inspiration. FIG. 43C shows a real image of the woman in a state of starting breath holding. FIG. 43D shows a real image of the woman in an expiration state upon completion of breath holding. Face marks schematically indicating an inspiration state, breath holding state, and expiration state, respectively, are displayed together with these real images. In addition, the remaining times of breath holding are displayed in three stages, namely, "more than 10 sec", "10 sec or less", and "five sec or less".

FIG. 44 shows an example of an image indicating the progress of examination. This example shows a state in which a subject to be examined is inserted into the gantry from the foot side using a top slide and the insertion posture of the subject with her arms being held up to her head.

Figure 32:
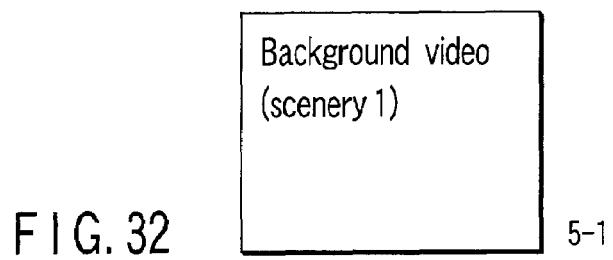
FIG. 32 is a view showing still another example of the display item stored in the display item storage unit in FIG. 16.
Figure 33:
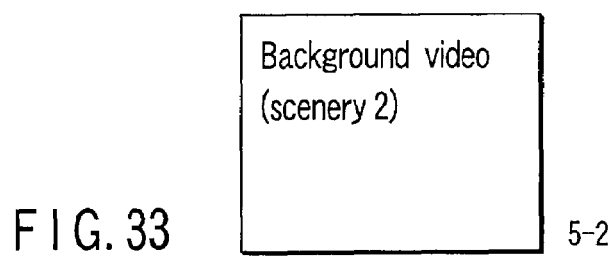
FIG. 33 is a view showing still another example of the display item stored in the display item storage unit in FIG. 16.
Figure 34:
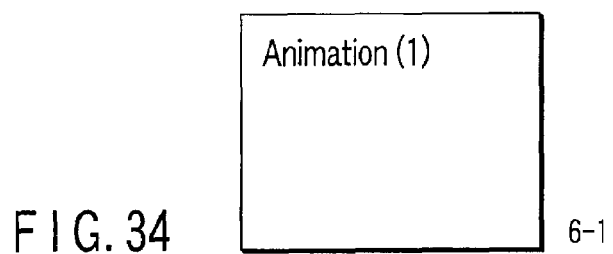
FIG. 34 is a view showing still another example of the display item stored in the display item storage unit in FIG. 16.
Figure 35:
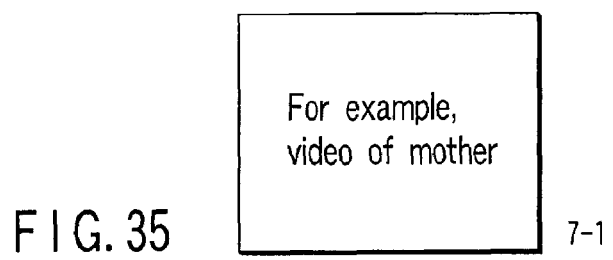
FIG. 35 is a view showing still another example of the display item stored in the display item storage unit in FIG. 16.
Figure 36:
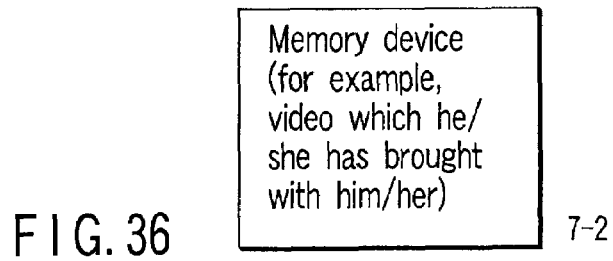
FIG. 36 is a view showing still another example of the display item stored in the display item storage unit in FIG. 16.

Furthermore, image files include, for example, the files of background videos (FIGS. 32 and 33) of sceneries prepared in advance as video files having relaxing effects regardless of examination instructions. Image files also include the file of animation (FIG. 34) aimed at infants and children in particular to suppress their body movement and keep them quiet during examination and the file of a video of a mother (FIG. 35) which is captured in advance or captured live by a TV camera 2210. In addition, it suffices to play back a favorite video stored in a memory device 2209 which the subject himself/herself has brought with him/her.

As described above, an audio file is played back in accordance with an examination stage under the control of the display/loudspeaker control unit 2205, and the operator can cancel the automatic mode of displaying image files and select, as an audio or image source through the operation device 2115, the memory device 2209, the TV camera 2210, or a microphone 2211 which is connected through an input interface 2207 and a connection terminal 2208. For example, displaying the selection window shown in FIG. 37 allows to receive, from the subject, an instruction to select audio data or video data at the time of relaxing before the start of examination.

The connection terminal 2208 is a general purpose standard terminal, which allows the subject to bring the memory device 2209 with him/her to a hospital upon checking his/her favorite music or video and play it back. Alternatively, selecting the TV camera 2210 and the microphone 2211, which are placed in an operation room near an imaging room, as sources makes it possible to, for example, show a video of a mother to her child or infant and give him/her various kinds of instructions by voice.

Figure 19:
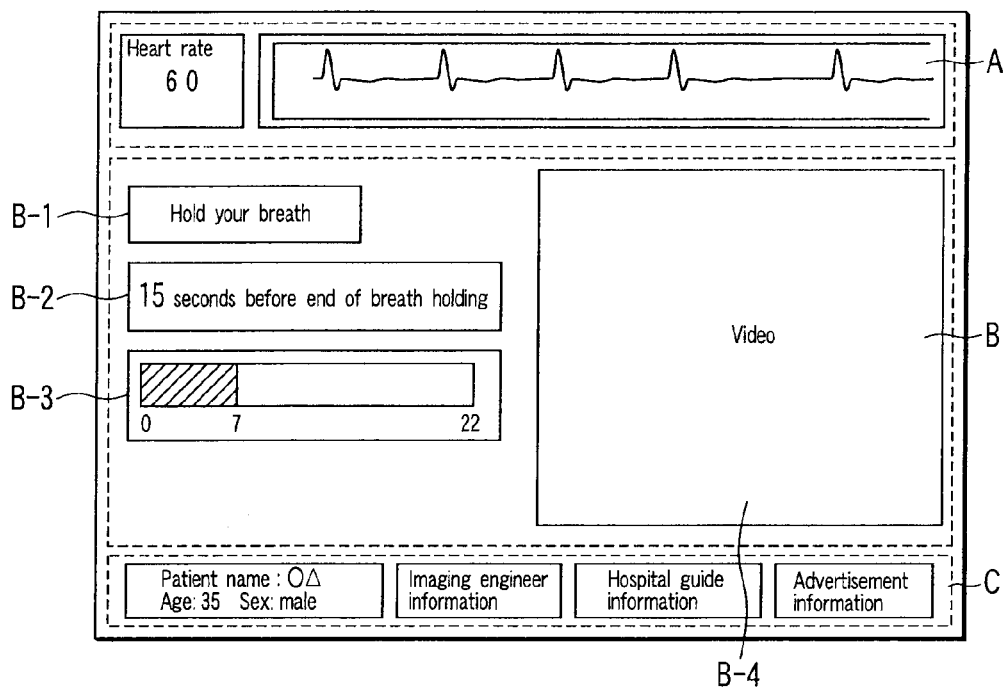
FIG. 19 is a view showing an example of a display window on a gantry mount display comprising a display window forming unit in FIG. 16.

FIGS. 19 and 20 show window examples on the gantry mount display 2201 at the time of breath holding. When performing breath-holding examination, this apparatus plays back an audio file containing the message "hold your breath" and displays a plurality of image files B-1, B-2, B-3, and B-4 associated with the audio file. The apparatus displays, for example, the video B-5 corresponding to a breath holding instruction aimed at an infant, as shown in FIG. 20.

Note that the window on the gantry mount display 2201 can be divided into a display area B aimed at the subject, an area A aimed at the operator (imaging engineer), and an area C aimed at both the subject and the operator. The display area A displays a heart rate, electrocardiographic waveform, and the like. The display area C displays patient information, imaging engineer information, hospital guide information, and advertisement information.

This embodiment allows the subject to easily understand which actions he/she should take at various timings during examination, through voice and image. The subject can therefore properly take actions, e.g., breath holding. In addition, since operators can easily change display contents and voice contents, subjects can further easily understand which actions they should take in accordance with the characteristics of facilities which they use. Furthermore, since the remaining time of breath holding, the time to the next scan, the remaining scheduled time of examination, and the like can be displayed, the anxiety of the patent can be relieved. Timely supplying audio and video data which promote relaxation can promote the relaxation of the subject and stabilize examination. In addition, this embodiment allows to designate a device to be used among the microphone 2211, TV camera 2210, memory device 2209, and the like which are freely connected to the connection terminal 2208, as an audio or video source, in addition to the storage units 2212 and 2213, and hence can effectively promote relaxation in accordance with personal preferences.

This embodiment can be modified as follows. As shown in FIG. 45, the gantry mount display 2201, the loudspeaker unit 2202, the display/loudspeaker control unit 2205, the display item storage unit 2212, and the audio item storage unit 2213 constitute a system (user navigation system or respiration navigation system) 3000 independent of the X-ray CT apparatus, together with a designation unit 2214 and an editing unit 2215. The display/loudspeaker control unit 2205, display item storage unit 2212, audio item storage unit 2213, and editing unit 2215 are accommodated in a gantry 2100. The designation unit 2214 is mounted on the housing of the gantry 2100 or is connected to it through a connector.

The user navigation system 3000 is connected to the X-ray CT apparatus through a plug 3001. Upon receiving a control signal from the scan controller 2110 of the X-ray CT apparatus, the display/loudspeaker control unit 2205 of the user navigation system 3000 reads out the image file and audio file (to be generically termed as respiration guide data files) specified by the control signal from the display item storage unit 2212 and the audio item storage unit 2213. The display/loudspeaker control unit 2205 then causes the gantry mount display 2201 to perform display, and causes the loudspeaker unit 2202 to perform audio output.

The designation unit 2214 is an operation device which the user uses to designate the insertion direction of a subject to be examined into the gantry of the X-ray computed tomographic apparatus, whether to raise or lower his/her arms, whether to use a contrast medium, and the type of respiration method to be used. A respiration guide data file editing unit is provided to edit respiration guide data files in accordance with the insertion direction, whether to raise or lower the arms, whether to use a contrast medium, and the type of respiration method to be used which are designated through the designation unit 2214.

Figure 46:
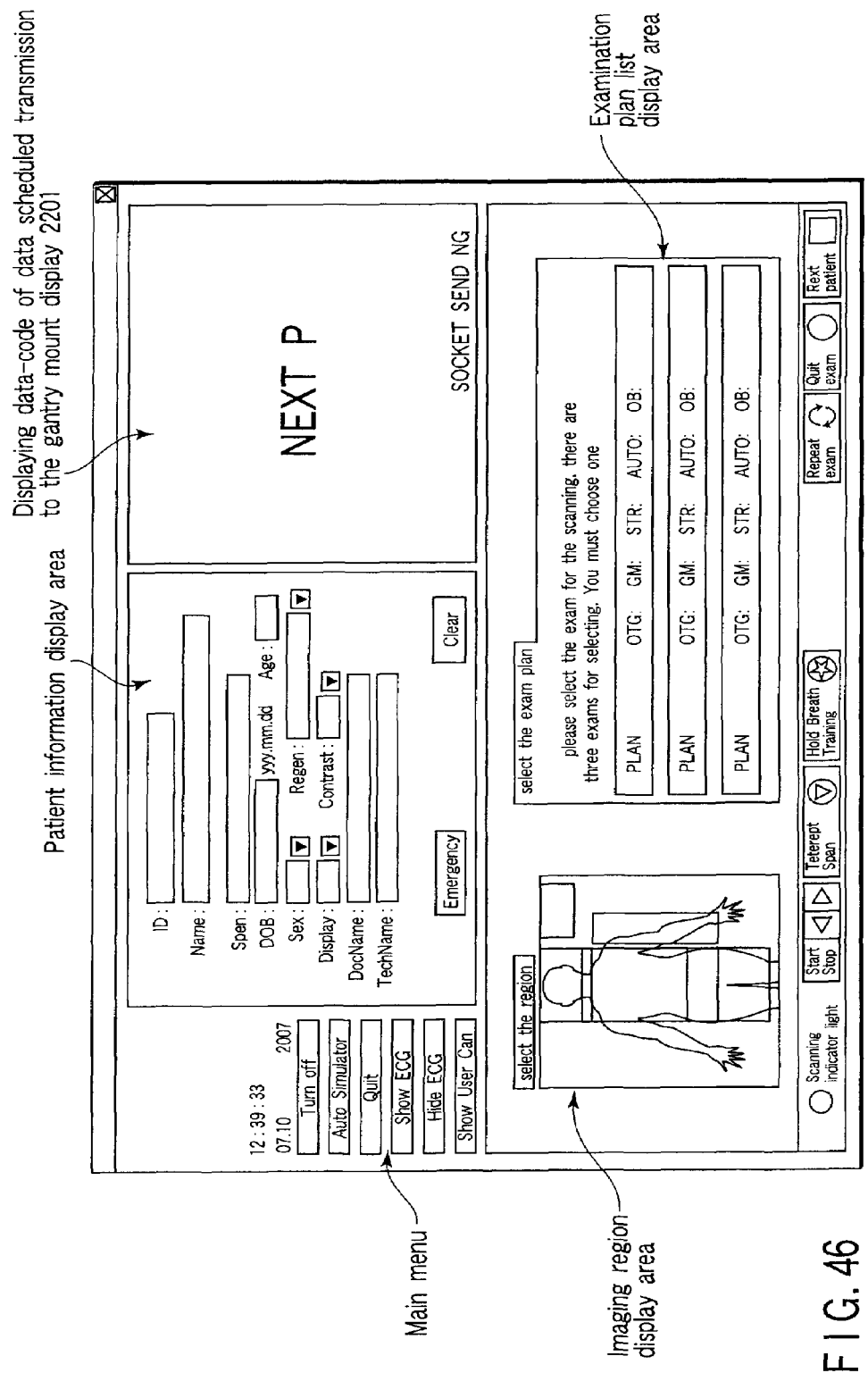
FIG. 46 is a view showing an example of an examination information window displayed on the screen of the display device or operation device of the X-ray CT apparatus in FIG. 45.

FIG. 46 shows an examination information window displayed on the screen of a display device 2116 of the X-ray CT apparatus or the operation device 2115. This window displays the information of a control signal transmitted from the scan controller 2110 of the X-ray CT apparatus to the user navigation system 3000. The information of a control signal includes a data code as information which specifies a display item and an audio item, the time of generation of the control signal, the type of control signal, and information indicating the results of execution of display and audio item outputs. The operator can check the display item displayed on the gantry mount display 2201 and the audio item output from the loudspeaker unit 2202 by seeing the information of the control signal.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomographic apparatus comprising:
a gantry including an X-ray tube which generates X-rays and an X-ray detector which detects X-rays transmitted through a subject to be examined;
a tomogram generating unit which generates tomogram data on the basis of an output from the X-ray detector;
a cardiac index calculating unit which instantly calculates a plurality of cardiac indexes associated with a heartbeat state on the basis of an electrocardiogram associated with the subject;
a cardiac index selection unit which selects at least one cardiac index among the plurality of calculated cardiac indexes in accordance with a user instruction;
a display unit which is held on a housing of the gantry directly or through an arm and instantly displays the selected cardiac index and at the same time displays an instruction to the subject, and
an operation window generating unit which generates an operation window for selection of the cardiac index and design of a display layout,
wherein the operation window includes an electrocardiographic area in which the user can select the at least cardiac index for display and a second area for display of information corresponding to progress of examination as selected by the user, and the operation window generating unit is operable by the user to control the display layout of the electrocardiographic area and the second area.

2. An apparatus according to claim 1, wherein the display unit displays the electrocardiogram together with the cardiac index.

3. An apparatus according to claim 1, wherein the cardiac index calculating unit calculates a heart rate, an interval average heart rate, and a difference between an interval average heart rate and a heart rate as the cardiac indexes.

* * * * *